US012037585B2

(12) United States Patent
Khvorova et al.

(10) Patent No.: US 12,037,585 B2
(45) Date of Patent: Jul. 16, 2024

(54) OLIGONUCLEOTIDES FOR TISSUE SPECIFIC GENE EXPRESSION MODULATION

(71) Applicant: UNIVERSITY OF MASSACHUSETTS, Boston, MA (US)

(72) Inventors: Anastasia Khvorova, Westborough, MA (US); Chantal Ferguson, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 54 days.

(21) Appl. No.: 17/132,803

(22) Filed: Dec. 23, 2020

(65) Prior Publication Data
US 2021/0340533 A1    Nov. 4, 2021

Related U.S. Application Data

(60) Provisional application No. 62/953,011, filed on Dec. 23, 2019.

(51) Int. Cl.
*C12N 15/113*    (2010.01)
*A61K 47/54*    (2017.01)

(52) U.S. Cl.
CPC .......... *C12N 15/113* (2013.01); *A61K 47/542* (2017.08); *A61K 47/549* (2017.08);
(Continued)

(58) Field of Classification Search
CPC ... A61P 25/28; C12N 15/113; C12N 2310/14; C12N 2310/315; C12N 2310/322;
(Continued)

(56) References Cited

U.S. PATENT DOCUMENTS 4,522,811 A    6/1985 Eppstein et al.
5,328,470 A    7/1994 Nabel et al.
(Continued)

FOREIGN PATENT DOCUMENTS

WO    WO 2003/029459 A2    4/2003
WO    WO-2010129799 A2 *  11/2010 .......... A61K 31/713
(Continued)

OTHER PUBLICATIONS

Alterman et al. (Nature Biotechnology, vol. 37, Aug. 2019, pp. 884-894).*
(Continued)

*Primary Examiner* — Terra C Gibbs
(74) *Attorney, Agent, or Firm* — LATHROP GPM LLP; James H. Velema, Esq.; Michael J. Spellberg

(57) ABSTRACT

This disclosure relates to a therapeutic combination of drugs for the treatment or management of a neurodegenerative disease, the combination comprising: a first conjugate comprising an RNA silencing agent and a first targeting agent that targets the first conjugate to the central nervous system, and a second conjugate comprising an antagonist of the RNA silencing agent and a second targeting agent that targets the second conjugate to a off-target tissue.

15 Claims, 26 Drawing Sheets

Specification includes a Sequence Listing.

(52) U.S. Cl.
CPC ........ *A61K 47/554* (2017.08); *C12N 2310/14* (2013.01); *C12N 2310/315* (2013.01); *C12N 2310/322* (2013.01); *C12N 2310/3515* (2013.01); *C12N 2320/32* (2013.01)

(58) Field of Classification Search
CPC ...... C12N 2310/346; C12N 2310/3515; C12N 2320/31; A61K 47/542
See application file for complete search history.

(56) References Cited

U.S. PATENT DOCUMENTS

| | | | |
|---|---|---|---|
| 5,684,143 | A | 11/1997 | Gryaznov et al. |
| 5,814,014 | A | 9/1998 | Elsberry et al. |
| 5,858,988 | A | 1/1999 | Wang |
| 6,093,180 | A | 7/2000 | Elsberry |
| 6,107,094 | A | 8/2000 | Crooke |
| 6,168,587 | B1 | 1/2001 | Bellhouse et al. |
| 6,177,403 | B1 | 1/2001 | Stedman |
| 6,194,389 | B1 | 2/2001 | Johnston et al. |
| 6,291,438 | B1 | 9/2001 | Wang |
| 6,471,996 | B1 | 10/2002 | Sokoll et al. |
| 6,472,375 | B1 | 10/2002 | Hoon et al. |
| 7,459,547 | B2 | 12/2008 | Zamore et al. |
| 7,732,593 | B2 | 6/2010 | Zamore et al. |
| 7,750,144 | B2 | 7/2010 | Zamore et al. |
| 7,772,203 | B2 | 8/2010 | Zamore et al. |
| 8,304,530 | B2 | 11/2012 | Zamore et al. |
| 8,309,704 | B2 | 11/2012 | Zamore et al. |
| 8,309,705 | B2 | 11/2012 | Zamore et al. |
| 8,329,892 | B2 | 12/2012 | Zamore et al. |
| 8,431,544 | B1 | 4/2013 | Agrawal et al. |
| 2005/0220766 | A1 | 10/2005 | Amalfitano et al. |
| 2005/0245475 | A1* | 11/2005 | Khvorova .......... C12N 15/1138 536/23.1 |
| 2006/0078542 | A1 | 4/2006 | Mah et al. |
| 2007/0259827 | A1 | 11/2007 | Aronin et al. |
| 2008/0269149 | A1 | 10/2008 | Bowles et al. |
| 2010/0186103 | A1 | 7/2010 | Gao et al. |
| 2014/0296486 | A1 | 10/2014 | Gao et al. |
| 2016/0024505 | A1 | 1/2016 | Collard et al. |
| 2016/0089453 | A1 | 3/2016 | Zamore et al. |
| 2016/0319279 | A1 | 11/2016 | Hutvagner et al. |
| 2017/0037404 | A1† | 2/2017 | Brown et al. |
| 2018/0153833 | A1 | 6/2018 | Tavazoie et al. |
| 2019/0247507 | A1 | 8/2019 | Khvorova et al. |

FOREIGN PATENT DOCUMENTS

| | | | | |
|---|---|---|---|---|
| WO | 2016/100716 | A1 † | 6/2016 | |
| WO | WO-2016100716 | A1 * | 6/2016 | .............. A61P 43/00 |
| WO | WO 2021/133941 | A1 | 7/2021 | |

OTHER PUBLICATIONS

Alisky et al., "Gene Therapy for Amyotrophic Lateral Sclerosis and Other Motor Neuron Diseases", Human Gene Therapy, vol. 11, Issue 17, pp. 2315-2329, Jul. 6, 2004.

Alvarez-Erviti et al., "Delivery of siRNA to The Mouse Brain by Systemic Injection of Targeted Exosomes", Nature Biotechnology, vol. 29, No. 4, pp. 341-345, Apr. 2011.

Ambros et al., "MicroRNAs and Other Tiny Endogenous RNAs in C. elegans", Current Biology, vol. 13, Issue 10, pp. 807-818, May 13, 2003.

Atwell et al., "Stable Heterodimers From Remodeling The Domain Interface of a Homodimer Using a Phage Display Library", Journal of Molecular Biology, vol. 270, Issue 1, pp. 26-35, Jul. 4, 1997.

Bell, et al., "Liposomal Transfection Efficiency and Toxicity on Glioma Cell Lines: In Vitro and In Vitro Studies", Neuroreport, vol. 9, Issue 5, pp. 793-798, Mar. 3, 1998.

Billy et al., "Specific Interference With Gene Expression Induced by Long, Double-Stranded RNA In Mouse Embryonal Teratocarcinoma Cell Lines", Proceedings of the National Academy of Sciences, vol. 98, No. 25, pp. 14428-14433, Dec. 4, 2001.

Braasch et al., "RNA Interference in Mammalian Cells by Chemically-Modified RNA", Biochemistry, vol. 42, No. 26, pp. 7967-7975, Jun. 11, 2003.

Brummelkamp et al., "A System for Stable Expression of Short Interfering RNAs in Mammalian Cells", Science, vol. 296, Issue 5567, pp. 550-553, Apr. 19, 2002.

Byrne et al., "Novel Hydrophobically Modified Asymmetric RNAi Compounds (sd-rxRNA) Demonstrate Robust Efficacy in the Eye", Journal of Ocular Pharmacology and Therapeutics, vol. 29, Issue 10, pp. 855-864, Dec. 3, 2013.

Carter, "Handbook of Parvoviruses", ed., P. Tijsser, CRC Press, pp. 155-168, 1990.

Chen et al., "Gene Therapy for Brain Tumors: Regression of Experimental Gliomas by Adenovirus-Mediated Gene Transfer In Vivo", Proceedings of the National Academy of Sciences, vol. 91, No. 8, pp. 3054-3057, Apr. 1994.

Cheng, et al., "Enhanced Hepatic Uptake and Bioactivity of Type $\alpha 1(I)$ Collagen Gene Promoter-Specific Triplex-Forming Oligonucleotides after Conjugation with Cholesterol", Journal of Pharmacology and Experimental Therapeutics, vol. 317, Issue 2, pp. 797-805, Aug. 2019.

Dass, "Cytotoxicity Issues Pertinent to Lipoplex-Mediated Gene Therapy In-Vivo", Journal of Pharmacy and Pharmacology, vol. 54, Issue 5, pp. 593-601, Feb. 18, 2010.

Davidson et al., "A Model System for In Vivo Gene Transfer Into The Central Nervous System Using an Adenoviral Vector", Nature Genetics, vol. 3, No. 3, pp. 219-223, Mar. 1993.

Davidson et al., "Recombinant Adeno-Associated Virus Type 2, 4, and 5 Vectors: Transduction of Variant Cell Types and Regions In The Mammalian Central Nervous System", Proceedings of the National Academy of Sciences, vol. 97, No. 7, pp. 3428-3432, Mar. 28, 2000.

Doench et al., "siRNAs Can Function as miRNAs", Genes & Development, vol. 17, pp. 438-442, 2003.

Ducruix et al., "Crystallization of Nucleic Acids and Proteins: A Practical Approach", Second Edition, Oxford University Press, New York, pp. 201-216, 1999.

Eckstein, "Phosphorothioate Oligodeoxynucleotides: What Is Their Origin and What Is Unique About Them?", Antisense and Nucleic Acid Drug Development, vol. 10, Issue 2, pp. 117-121, 2000.

Egusquiaguirre et al., "Nanoparticle Delivery Systems for Cancer Therapy: Advances In Clinical and Preclinical Research", Clinical and Translational Oncology, vol. 14, pp. 83-93, 2012.

El-Andaloussi et al., "Exosome-Mediated Delivery of siRNA In Vitro and In Vivo", Nature Protocols, vol. 7, No. 12, pp. 2112-2126, Nov. 15, 2012.

El-Andaloussi et al., "Exosomes for Targeted siRNA Delivery Across Biological Barriers", Advanced Drug Delivery Reviews, vol. 65, pp. 391-397, 2013.

El-Andaloussi et al., "Extracellular Vesicles: Biology and Emerging Therapeutic Opportunities", Nature Reviews Drug Discovery, vol. 12, pp. 347-357, May 2013.

Elmen et al., "Locked Nucleic Acid (LNA) Mediated Improvements in siRNA Stability and Functionality", Nucleic Acids Research, vol. 33, Issue 1, pp. 439-447, Jan. 14, 2005.

Fattal et al., "Biodegradable Polyalkylcyanoacrylate Nanoparticles for The Delivery of Oligonucleotides", Journal of Controlled Release, vol. 53, pp. 137-143, May 1998.

Fisher et al., "Transduction With Recombinant Adeno-Associated Virus for Gene Therapy Is Limited by Leading-Strand Synthesis", Journal of virology, vol. 70, No. 1, pp. 520-532, 1996.

Godard et al., "Antisense Effects of Cholesterol-Oligodeoxynucleotide Conjugates Associated with Poly(alkylcyanoacrylate) Nanoparticles", European Journal of Biochemistry banner, vol. 232, pp. 404-410, 1995.

Goodson, "Dental Applications, Medical Applications of Controlled Release", vol. 2, pp. 115-138, Jan. 1, 1984.

Grad et al., "Computational and Experimental Identification of C. elegans microRNAs", Molecular Cell, vol. 11, Issue 5, pp. 1253-1263, May 2003.

(56) References Cited

OTHER PUBLICATIONS

Griffiths-Jones, "The microRNA Registry", Nucleic Acids Research, vol. 32, Issue Supplement 1, pp. D109-D111, 2004.
Hamajima et al., "Intranasal Administration of HIV-DNA Vaccine Formulated with a Polymer, Carboxymethylcellulose, Augments Mucosal Antibody Production and Cell-Mediated Immune Response", Clinical Immunology and Immunopathology, vol. 88, Issue 2, pp. 205-210, Aug. 1, 1998.
Herdewijn "Heterocyclic Modifications of Oligonucleotides and Antisense Technology", Antisense and Nucleic Acid Drug Development, vol. 10, Issue 4, pp. 297-310, Jul. 8, 2004.
Hutvagner et al., "A microRNA in a Multiple-Turnover RNAi Enzyme Complex", Science, vol. 297, Issue 5589, pp. 2056-2060, Sep. 20, 2002.
International Search Report & Written Opinion Received for PCT Application No. PCT/US2020/066891, dated Apr. 30, 2021.
Karlin et al., "Applications and Statistics for Multiple High-Scoring Segments In Molecular Sequences", Proceedings of the National Academy of Sciences of the USA, vol. 90, pp. 5873-5877, Jun. 1, 1993.
Karlin et al., "Methods for Assessing The Statistical Significance of Molecular Sequence Features by Using General Scoring Schemes", Proceedings of the National Academy of science of the USA, vol. 87, No. 6, pp. 2264-2268, Mar. 1, 1990.
Lagos-Quintana et al., "Identification of Novel Genes Coding for Small Expressed RNAs", Science, vol. 294, Issue 5543, pp. 853-858, Oct. 26, 2001.
Lagos-Quintana et al., "Identification of Tissue-Specific MicroRNAs from Mouse", Current Biology, vol. 12, Issue 9, pp. 735-739, Apr. 30, 2002.
Lagos-Quintana et al., "New microRNAs From Mouse and Human", RNA, vol. 9, No. 2, pp. 175-179, 2003.
Lai et al., "Computational Identification of *Drosophila* microRNA Genes", Genome Biology, vol. 4, No. 7, pp. 1-20, Jun. 30, 2003.
Lam et al., "A New Type of Synthetic Peptide Library for Identifying Ligand-Binding Activity", Nature, vol. 354, pp. 82-84, Nov. 7, 1991.
Lambert et al., "Nanoparticulate Systems for The Delivery of Antisense Oligonucleotides", Advanced Drug Delivery Reviews, vol. 47, pp. 99-112, 2001.
Lau et al., "An Abundant Class of Tiny RNAs with Probable Regulatory Roles in Caenorhabditis elegans", Science, vol. 294, Issue 5543, pp. 858-862, Oct. 26, 2001.
Lee et al., "An Extensive Class of Small RNAs in Caenorhabditis elegans", Science, vol. 294, Issue 5543, pp. 862-864, Oct. 26, 2001.
Lee et al., "Recent Developments In Nanoparticle-Based siRNA Delivery for Cancer Therapy", BioMed Research International, vol. 2013, Article ID 782041, 10 Pages, Jun. 2013.
Lim et al., "The microRNAs of Caenorhabditis elegans", Genes & Development, vol. 17, No. 8, pp. 991-1008, 2003.
Lim et al., "Vertebrate MicroRNA Genes", Science, vol. 299, Issue 5612, p. 1540, Mar. 7, 2003.
Masotti et al., "Comparison of Different Commercially Available Cationic Liposome-DNA Lipoplexes: Parameters Influencing Toxicity and Transfection Efficiency", Colloids and Surfaces B: Biointerfaces, vol. 68, Issue 2, pp. 136-144, Feb. 2009.
McCaffrey et al., "Gene Expression: RNA Interference in Adult Mice", Nature, vol. 418, No. 6893, pp. 38-39, Jul. 4, 2002.
Miyagishi et al., "U6 promoter-driven siRNAs With Four Uridine 3' Overhangs Efficiently Suppress Targeted Gene Expression In Mammalian Cells", Nature Biotechnology, vol. 20, No. 5, pp. 497-500, May 1, 2002.
Mourelatos et al., "miRNPs: A Novel Class of Ribonucleoproteins Containing Numerous microRNAs", Genes & Development, vol. 16, No. 6, pp. 720-728, 2002.
Nielsen et al., "Sequence-Selective Recognition of DNA by Strand Displacement With a Thymine-Substituted Polyamide", Science, vol. 254, Issue 5037, pp. 1497-1500, Dec. 1991.
Petersen et al., "LNA: A Versatile Tool for Therapeutics and Genomics", Trends in Biotechnology, vol. 21, Issue 2, pp. 74-81, Feb. 2003.
Putnam, "Antisense Strategies and Therapeutic Applications", American Journal of Health System Pharmacy, vol. 53, No. 2, pp. 151-160, Jan. 15, 1996.
Reinhart et al., "Small RNAs Correspond to Centromere Heterochromatic Repeats", Science, vol. 297, No. 5588, 1 Page, Sep. 13, 2002.
Rusckowski et al., "Biodistribution and Metabolism of a Mixed Backbone Oligonucleotide (GEM 231) Following Single and Multiple Dose Administration in Mice", Antisense and Nucleic Acid Drug Development, vol. 10, Issue 5, pp. 333-345, Oct. 2000.
Schwab et al., "An Approach for New Anticancer Drugs: Oncogene-Targeted Antisense DNA", Annals of Oncology, vol. 5, Issue 4, pp. 55-58, 1994.
Soutschek et al., "Therapeutic Silencing of an Endogenous Gene by Systemic Administration of Modified siRNAs", Nature, vol. 432, No. 7014, pp. 173-178, Nov. 11, 2004.
Stein et al., "Inhibition of Vesivirus Infections in Mammalian Tissue Culture With Antisense Morpholino Oligomers", Antisense and Nucleic Acid Drug Development, vol. 11, No. 5, pp. 317-325, Oct. 2001.
Stein et al., "Systemic and Central Nervous System Correction of Lysosomal Storage in Mucopolysaccharidosis Type VII Mice", Journal of Virology, vol. 73, No. 4, pp. 3424-3429, Apr. 1999.
Vorobjev et al., "Nuclease Resistance and RNase H Sensitivity of Oligonucleotides Bridged by Oligomethylenediol and Oligoethylene Glycol Linkers", Antisense and Nucleic Acid Drug Development, vol. 11, No. 2, pp. 77-85, Apr. 2011.
Wang et al., "Nanoparticle-Based Delivery System for Application of siRNA In Vivo", Current Drug Metabolism, vol. 11, No. 2, pp. 182-196, 2010.
Wright et al., "Identification of Factors That Contribute to Recombinant AAV2 Particle Aggregation and Methods to Prevent Its Occurrence During Vector Purification and Formulation", Molecular Therapy, vol. 12, Issue 1, pp. 171-178, Jul. 2005.
Xia et al., "siRNA-Mediated Gene Silencing in Vitro and In Vivo", Nature Biotechnology, vol. 20, No. 10, pp. 1006-1010, Sep. 16, 2002.
Yuan et al., "Recent Advances of siRNA Delivery by Nanoparticles", Expert Opinion on Drug Delivery vol. 8, Issue 4, pp. 521-536, 2011.
Zeng et al., "Both Natural and Designed Micro RNAs Can Inhibit the Expression of Cognate mRNAs When Expressed in Human Cells", Molecular Cell, vol. 9, pp. 1327-1333, Jun. 1, 2002.
Zeng et al., "Sequence Requirements for Micro RNA Processing and Function in Human Cells", RNA, vol. 9, pp. 112-123, 2003.
Zhang et al., "Several rAAV Vectors Efficiently Cross the Blood-brain Barrier and Transduce Neurons and Astrocytes in the Neonatal Mouse Central Nervous System", Molecular Therapy, vol. 19, Issue 8, pp. 1440-1448, Aug. 1, 2011.
Zou et al., "Liposome-Mediated NGF Gene Transfection Following Neuronal Injury: Potential Therapeutic Applications", Gene Therapy, vol. 6, No. 6, pp. 994-1005, Jun. 25, 1999.

\* cited by examiner
† cited by third party

| ID | Targeting sequence (30 BP) | Antisense sequence (5'-3') | Sense sequence (5'-3') |
|---|---|---|---|
| Mouse | | | |
| 1134 | TGTCCTGCAACAACATCCATATCCAGCCAGG | UUGGAUAUGGAUGUUGUUGCAG | GCAACAACAUCCAUAUCCAA |
| 1203 | CCTTGCTTAATAAAGATTCTCCGAGCACATT | UCUCGGAGAAUCUUUAUUAAGC | UUAAUAAAGAUUCUCCGAGA |
| Human | | | |
| 1156 | GTTTAATAAAGATTCACCAAGTTTCACGCA | UAAACUUGGUGAAUCUUUAU | GAUUCACCAAGUUUA |
| 1163 | GTTTAATAAAGATTCACCAAGTTTCACGCAAA | UUUGCGUGAAACUUGGUGAA | CAAGUUUCACGCAAA |

FIG. 3A

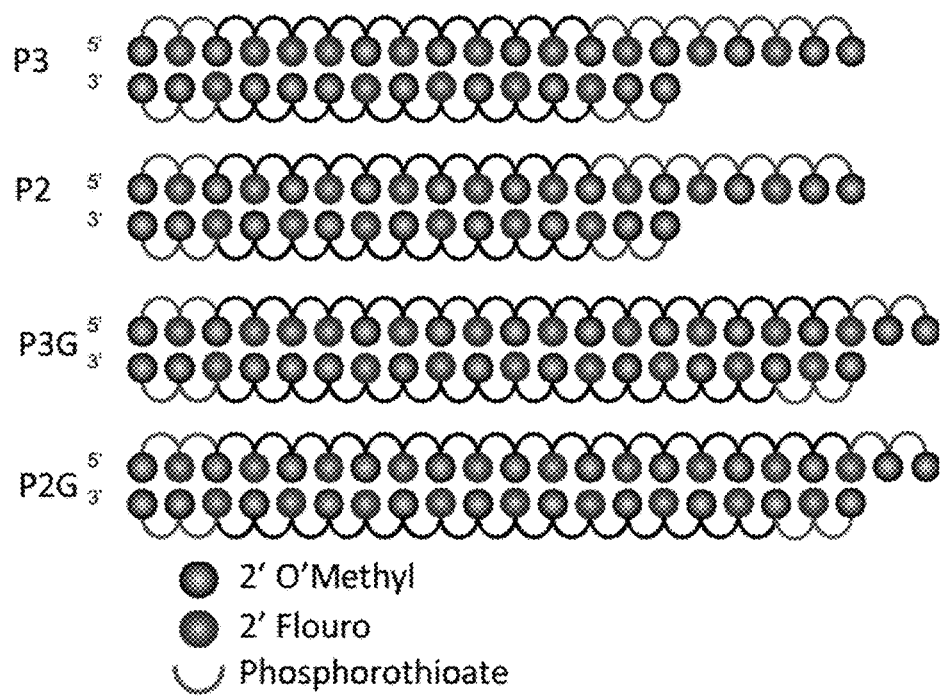

FIG. 3B

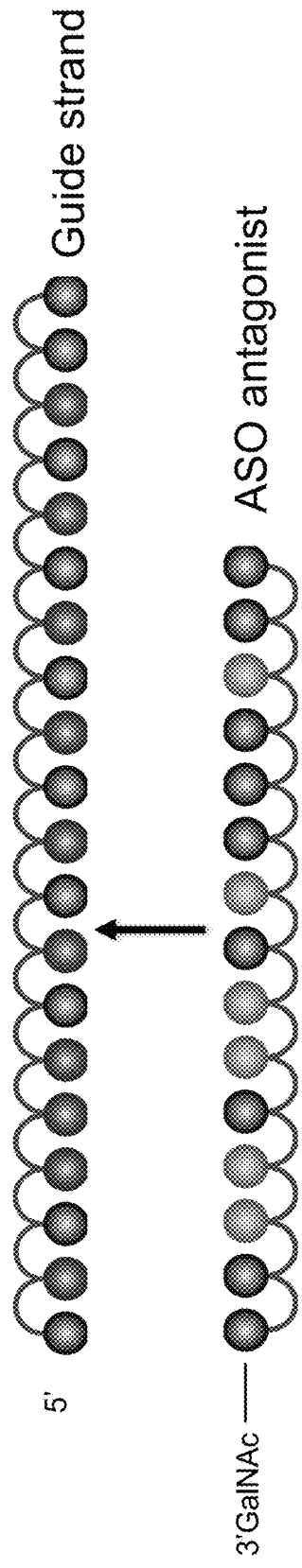

FIG. 13A

| Name | Modified sequence | Sequence (5'-30') |
|---|---|---|
| 1134 antagonist | (mA)#(A)#(mC)#(mA)#(mU)#(mC)#(mA)#(U)#(mA)#(C)#(mA)#(U)#(mC)#(mA)#(C)#(mA)PO(A)-GalNAc (C)#(mA)#(U)#(A)#(mU)#(mC)#(C)#(mA)#(mA)PO(A)-GalNAc | AACAUCCAUAUCCAA CAUAUCCAA |
| 1203 antagonist | (mA)#(A)#(mA)#(mG)#(mA)#(U)#(mC)#(U)#(mC)#(C)#(mG)#(A)#(mG)PO(A)-GalNAc (U)#(mC)#(U)#(mC)#(C)#(mG)#(A)#(mG)PO(A)-GalNAc | AAAGAUCUCCGAGA UCUCCGAGA |
| 1156 antagonist | (mG)#(A)#(mU)#(mU)#(mC)#(A)#(mC)#(C)#(mA)#(A)#(mG)#(U)#(mU)#(U)#(mA)PO(A)-GalNAc (mC)#(mC)#(A)#(A)#(mG)#(U)#(mU)#(U)#(mA)PO(A)-GalNAc | GAUUCACCAAGUUUA CCAAGUUUA |
| 1163 antagonist | (mC)#(A)#(mA)#(mG)#(mU)#(mU)#(mC)#(A)#(mC)#(mG)#(mC)#(A)#(A)#(A)PO(A)-GalNAc (mU)#(C)#(A)#(mC)#(mG)#(C)#(A)#(A)PO(A)-GalNAc | CAAGUUCACGCAAA UCACGCAAA |

FIG. 13B

OLIGONUCLEOTIDES FOR TISSUE SPECIFIC GENE EXPRESSION MODULATION

CROSS-REFERENCE TO RELATED APPLICATIONS

This application claims the benefit of U.S. Provisional Application Ser. No. 62/953,011, filed Dec. 23, 2019, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Aug. 16, 2022, is named 711117_UM9-243_ST25.txt and is 10,817 bytes in size.

FIELD OF THE INVENTION

This disclosure relates to the novel combination of an RNA silencing agent for silencing a target mRNA in one or more target tissues with a repressor of the RNA silencing agent to inhibit silencing of the target mRNA in one or more off-target tissues. The disclosure also relates to novel methods for treating and preventing diseases by silencing a target mRNA in a target tissue while inhibiting target mRNA silencing in off-target tissues.

BACKGROUND

Patients with neurodegenerative diseases including Alzheimer's disease (AD) and Amyotrophic Lateral Sclerosis (ALS) have limited treatment options. Abnormalities in cholesterol transport are consistently linked to neurodegeneration and worsening clinical symptoms in AD and ALS, making cholesterol transport a pathway of particular interest as a target for gene therapies.

Apolipoprotein E (ApoE) facilitates cholesterol transport in the systemic circulation and in the central nervous system (CNS). In human plasma and CNS, total ApoE levels and specific ApoE isoforms (i.e. E2, E3, E4) are associated with the onset and progression of AD and ALS. In addition, total ApoE levels in CNS have been found to be predictive of neurodegeneration progression.

Certain diseases are monogenic, making them ideal targets for oligonucleotide therapeutic intervention, e.g., RNA interference (RNAi). RNAi is a fundamental mechanism involving short double stranded RNA fragments that can be used to reprogram cellular machinery and silence and degrade targeted mRNA on demand. This technology is clinically advanced and has revolutionized the field of human functional genetics. Many different technologies have been explored for mRNA knockdown both as therapeutics and as tools for functional study, including viral based delivery of short hairpin RNAs (shRNAs), antisense oligonucleotides (ASOs), and naked or slightly modified siRNAs.

Unmodified siRNA ("naked siRNA") has been difficult to deliver to more sensitive cell lines and in vivo to tissue in the past. Although transfection reagents such as Lipofectamine can be used, there is a very narrow window within which it is efficacious and non-toxic, and it must be optimized independently for different batches of neurons to determine siRNA to lipid ratios necessary for comparable levels of silencing (Bell, H., Kimber, W. L., Li, M. & Whittle, I. R. Liposomal transfection efficiency and toxicity on glioma cell lines: in vitro and in vivo studies. *NeuroReport* 9, 793-798 (1998); Dass, C. R. Cytotoxicity issues pertinent to lipoplex-mediated gene therapy in-vivo. *Journal of Pharmacy and Pharmacology* 1-9 (2010); Masotti, A. et al. Comparison of different commercially available cationic liposome-DNA lipoplexes: Parameters influencing toxicity and transfection efficiency. *Colloids and Surfaces B: Biointerfaces* 68, 136-144 (2009); Zou, L. L. et al. Liposome-mediated NGF gene transfection following neuronal injury: potential therapeutic applications. *Gene Ther* 6, 994-1005 (1999)). Hydrophobically modified siRNAs have also been used as an alternative for cellular and brain delivery (Sah, Supra; Soutschek, J. et al. Therapeutic silencing of an endogenous gene by systemic administration of modified siRNAs. *Nature* 432, 173-178 (2004); Cheng, K., Ye, Z., Guntaka, R. V. & Mahato, R. I. Enhanced hepatic uptake and bioactivity of type alpha1(I) collagen gene promoter-specific triplex-forming oligonucleotides after conjugation with cholesterol. *Journal of Pharmacology and Experimental Therapeutics* 317, 797-805 (2006); Byrne, M. et al. Novel Hydrophobically Modified Asymmetric RNAi Compounds (sd-rxRNA) Demonstrate Robust Efficacy in the Eye. *Journal of Ocular Pharmacology and Therapeutics* 29, 855-864 (2013)), and some of these compounds have even made it to clinic.

In mice, global reduction of ApoE reduces pathological features of neurodegeneration, suggesting that non-selective modulating of ApoE may be one treatment approach for neurodegenerative diseases. It is possible that close-to complete modulation of ApoE is necessary to have a measurable effect on neurodegeneration, a distinctive feature of the presented compounds. Yet, total loss of ApoE in mice also causes atherosclerosis. The atherosclerosis is caused by systemic decreases in the ApoE levels.

Thus, CNS-selective modulation of ApoE expression may be a more viable therapy than complete ApoE silencing, and the conjugation of oligonucleotides to specific ligands (e.g., GalNAc, cholesterol) enables tissue specific delivery and efficacy of oligonucleotides. While some conjugated oligonucleotides deliver specifically to target tissues, others are less specific, and deliver to tissues other than the intended targets, often because they are cleared in these tissues. In many cases, minimal, non-specific delivery is tolerable; however, in many diseases, it is necessary to modulate gene expression in the intended target tissues, and only in that target tissue. In addition, no data evaluating tissue specific expression on neuro-pathology is currently available, nor are oligonucleotide sequences that exhibit a potent and efficacious silencing activity on ApoE expression.

SUMMARY

In one aspect, the disclosure provides a therapeutic combination of drugs for the treatment or management of a neurodegenerative disease, the combination comprising: a first conjugate comprising an RNA silencing agent and a first targeting agent that targets the first conjugate to the central nervous system, and a second conjugate comprising an antagonist of the RNA silencing agent and a second targeting agent that targets the second conjugate to a off-target tissue.

In an embodiment, the first conjugate and second conjugate are compounded together in a same unitary composition comprising both conjugates.

In an embodiment, the first conjugate and second conjugate are in separate pharmaceutical compositions.

In an embodiment, the RNA silencing agent inhibits the expression of Apoliprotein E (ApoE) gene in an organism.

In an embodiment, the RNA silencing agent comprises an RNA molecule comprising 15 to 35 bases in length, comprising a region of complementarity which is substantially complementary to 5' GUUUAAUAAAGAUUCACCAAGUUUCACGCAAA 3' (SEQ ID NO: 1).

In an embodiment, the RNA silencing agent comprises a region of complementarity which is substantially complementary to one or more of 5' GAUUCACCAAGUUUA 3' (SEQ ID NO: 2) and 5' CAAGUUUCACGCAAA 3' (SEQ ID NO: 3).

In an embodiment, the RNA molecule comprises single stranded (ss) RNA or double stranded (ds) RNA.

In an embodiment, the first conjugate comprises a Di-siRNA.

In an embodiment, the antagonist to the RNA silencing agent comprise a single-stranded oligonucleotide complementary to the guide strand of the siRNA of the first conjugate.

In an embodiment, the second conjugate comprises a GalNac-siRNA.

In an embodiment, the second targeting agent comprises a GalNac.

In an embodiment, the antagonist to the RNA silencing agent comprises one or more locked nucleic acids.

In an embodiment, the antagonist to the RNA silencing agent comprises 8 to 20 bases in length. In an embodiment, the antagonist to the RNA silencing agent comprises 8 bases in length. In an embodiment, the antagonist to the RNA silencing agent comprises 15 bases in length.

In an embodiment, the off-target tissue comprises a clearance tissue. In an embodiment, the off-target tissue comprises one or more of liver tissue, kidney tissue, and spleen tissue.

In one aspect, the disclosure provides a method treating, suppressing, or reducing severity of a of a neurodegenerative disease in a subject, the method comprising administering to the subject a therapeutically effective amount of the combination recited above.

In one aspect, the disclosure provides method of treating, suppressing, or reducing severity of a of a neurodegenerative disease in a subject, the method comprising administering to the subject a therapeutic combination of drugs, the combination comprising: a first conjugate comprising an RNA silencing agent and a first targeting agent that targets the first conjugate to a central nervous system, and a second conjugate comprising an antagonist of the RNA silencing agent and a second targeting agent that targets the second conjugate to a tissue outside the central nervous system, to block the action of the first conjugate outside the central nervous system.

In an embodiment, the first conjugate is administered to the subject prior to the second conjugate, concurrently with the second conjugate, or after the second conjugate.

In an embodiment, the neurodegenerative disease is a disorder caused, in whole or in part, by abnormalities in cholesterol transport.

In an embodiment, the neurodegenerative disease comprises one or more of amyotrophic lateral disease (ALS) and Alzheimer's disease (AD).

In an embodiment, the RNA silencing agent inhibits expression of Apolipoprotein E (ApoE) gene in the central nervous system and the second conjugate maintains cholesterol homeostasis.

In an embodiment, the RNA silencing agent is an RNA molecule comprising 15 to 35 bases in length, comprising a region of complementarity which is substantially complementary to 5' GUUUAAUAAAGAUUCACCAAGUUUCACGCAAA 3' (SEQ ID NO: 1).

In an embodiment, the RNA silencing agent comprises a region of complementarity which is substantially complementary to one or more of 5' GAUUCACCAAGUUUA 3' (SEQ ID NO: 2) and 5' CAAGUUUCACGCAAA 3' (SEQ ID NO: 3).

In an embodiment, the RNA molecule comprises single stranded (ss) RNA or double stranded (ds) RNA.

In an embodiment, the first conjugate comprises a Di-siRNA.

In an embodiment, the RNA silencing agent comprises a single-stranded oligonucleotide complementary to the guide strand of the siRNA of the first conjugate.

In an embodiment, the second conjugate comprises an antagonist of the RNA silencing agent and a second targeting agent that targets the second conjugate to an off-target tissue.

In an embodiment, the second conjugate comprises a GalNac-siRNA.

In an embodiment, the second targeting agent comprises a GalNac.

In an embodiment, the antagonist to the RNA silencing agent comprises one or more locked nucleic acids.

In an embodiment, the antagonist to the RNA silencing agent comprises 8 to 20 bases in length. In an embodiment, the antagonist to the RNA silencing agent comprises 8 bases in length. In an embodiment, the antagonist to the RNA silencing agent comprises 15 bases in length.

In an embodiment, the tissue outside the central nervous system comprises a clearance tissue. In an embodiment, the tissue outside the central nervous system comprises one or more of liver tissue, kidney tissue, and spleen tissue.

In one aspect, the disclosure provides a kit for the treatment or management of a neurodegenerative disease, the kit comprising: a first pharmaceutically acceptable composition a first conjugate comprising an RNA silencing agent and a first targeting agent that targets the first conjugate to a central nervous system, a second pharmaceutically acceptable composition of a second conjugate comprising an antagonist of the RNA silencing agent and a second targeting agent that targets the second conjugate to a tissue outside the central nervous system, and instructions for the administration of the first composition and second composition for treatment of a neurodegenerative disease.

In one aspect, the disclosure provides a method of treating, suppressing, or reducing the severity of a of a neurodegenerative disease in a subject, the method comprising administering to the subject a therapeutically effective amount of an RNA silencing agent inhibiting the expression of a gene in a central nervous system, the improvement comprising administering to the subject a conjugate comprising an antagonist of the RNA silencing agent and a targeting agent that targets the conjugate to a liver, to selectively inhibit the RNA silencing agent in the liver.

In another aspect, the disclosure provides a combination comprising:
 a first conjugate comprising an RNA silencing agent and
  a first targeting agent that targets the first conjugate to
  a target tissue, and
 a second conjugate comprising an anti-RNA silencing
  agent and a second targeting agent that targets the
  second conjugate to an off-target tissue.

In an embodiment, the first conjugate and second conjugate are compounded together in a same unitary composition comprising both conjugates.

In an embodiment, the first conjugate and second conjugate are in separate pharmaceutical compositions.

In an embodiment, the RNA silencing agent comprises single stranded (ss) RNA or double stranded (ds) RNA.

In an embodiment, the first targeting agent comprises cholesterol, eicosapentaenoic acid (EPA), docosahexaenoic acid (DHA), or docosanoic acid (DCA).

In an embodiment, the RNA silencing agent comprises an siRNA comprising a guide strand with a 5' end and a 3' end and a passenger strand with a 5' end and a 3' end.

In an embodiment, the first targeting agent is conjugated to the passenger strand 3' end.

In an embodiment, the first targeting comprises cholesterol, EPA, DHA, or DCA.

In an embodiment, the anti-RNA silencing agent comprises a single-stranded oligonucleotide sufficiently complementary to the RNA silencing agent.

In an embodiment, the anti-RNA silencing agent comprises a single-stranded oligonucleotide sufficiently complementary to the guide strand of the siRNA.

In an embodiment, the second targeting agent comprises a GalNAc.

In an embodiment, the anti-RNA silencing agent comprises one or more locked nucleic acids. In an embodiment, the anti-RNA silencing agent comprises one or more 2'-methoxy nucleotide modifications. In an embodiment, the anti-RNA silencing agent comprises one or more phosphorothioate linkages. In an embodiment, all internucleotide linkages in the anti-RNA silencing agent comprises phosphorothioate linkages.

In an embodiment, the anti-RNA silencing agent comprises 8 to 20 bases in length. In an embodiment, the anti-RNA silencing agent comprises 8 bases in length. In an embodiment, the anti-RNA silencing agent comprises 9 bases in length. In an embodiment, the anti-RNA silencing agent comprises 10 bases in length. In an embodiment, the anti-RNA silencing agent comprises 11 bases in length. In an embodiment, the anti-RNA silencing agent comprises 12 bases in length. In an embodiment, the anti-RNA silencing agent comprises 13 bases in length. In an embodiment, the anti-RNA silencing agent comprises 14 bases in length. In an embodiment, the anti-RNA silencing agent comprises 15 bases in length. In an embodiment, the anti-RNA silencing agent comprises 16 bases in length. In an embodiment, the anti-RNA silencing agent comprises 17 bases in length. In an embodiment, the anti-RNA silencing agent comprises 18 bases in length. In an embodiment, the anti-RNA silencing agent comprises 19 bases in length. In an embodiment, the anti-RNA silencing agent comprises 20 bases in length.

In an embodiment, the off-target tissue comprises a clearance tissue.

In an embodiment, the off-target tissue comprises one or more of liver tissue, kidney tissue, and spleen tissue.

In an embodiment, the target tissue comprises one or more of tissue in the central nervous system, muscle tissue, heart tissue, and lung tissue.

In another aspect, the disclosure provides a method of reducing off-target tissue silencing from an RNA silencing agent in a subject, the method comprising administering to the subject the first conjugate and second conjugate of any one of claims 38-59.

In an embodiment, the first conjugate and second conjugate are administered simultaneously.

In an embodiment, the first conjugate and second conjugate are administered sequentially.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 1A depicts a screen identifying hit sequences targeting ApoE in mouse primary astrocytes. FIG. 1B depicts dose response curves of hit sequences from the primary screen in mouse primary astrocytes. FIG. 1C depicts a dose response showing protein silencing in mouse primary astrocytes.

FIG. 2A depicts a screen identifying hit sequences targeting ApoE in HepG2 cells. FIG. 2B depicts dose response curves of hit sequences from the primary screen in HepG2 cells.

FIG. 3A illustrates oligonucleotides targeting ApoE. FIG. 3A depicts targeting sequences in the mouse and human ApoE genes and oligonucleotides targeting such sequences. FIG. 3A discloses SEQ ID NOS 39, 6-7, 40, 9-10, 35, 12, 48, 41, 14 and 49, respectively, in order of appearance. FIG. 3B illustrates example chemical modifications to the oligonucleotides.

FIG. 4A illustrates mRNA silencing in all regions of the brain 1-month post injection. FIG. 4B illustrates protein silencing in all regions of the brain 1-month post injection. FIG. 4C is a Western blot showing protein silencing throughout the brain.

FIG. 5A depicts a quantification of protein silencing in the hippocampus 1-month post injection. FIG. 5B is a Western blot showing target protein silencing.

FIG. 6A is a quantification of protein silencing in the spinal cord 1-month post injection.

FIG. 7A is a quantification of protein silencing in the liver 1-month post injection. FIG. 7B is a Western blot (ProteinSimple) showing target ApoE (37 kDa) protein silencing as compared to control vinculin (116 kDa).

FIG. 8A is a Western blot showing ApoE protein silencing in the liver vs. control vinculin. FIG. 8B is a Western blot showing no effect on the protein levels in the brain. FIG. 8C is a quantification of protein silencing in the liver and brain.

FIG. 9A depicts a quantification of total serum cholesterol after silencing CNS ApoE. FIG. 9B depicts a quantification of total serum cholesterol after silencing systemic ApoE. FIG. 9C depicts a quantification of cholesterol in LDL and HDL fractions after silencing systemic ApoE.

FIG. 10A illustrates protein silencing in the brain and liver after injection with CNS-siRNA$^{ApoE}$. FIG. 10B illustrates silencing in the brain (none) and liver after injection with GalNAc-siRNA$^{ApoE}$.

FIG. 11A exemplifies an siRNA conjugate A making its way to target organ A but also off-target organs B and C. FIG. 11B illustrates B/C-inhibitor suppressing the off-target activity of conjugate A.

FIGS. 13A-13B illustrate the action of an example antagonist of an RNA silencing agent. FIG. 13A is a schematic representation of the guide strand of a CNS-siRNAApoE (top) binding to the antagonist (bottom). The antagonist may contain locked nucleic acid modifications (LNA) that will enhance binding to the guide strand and prevent systemic silencing. FIG. 13B illustrates sequences of example antagonists of ApoE silencing agents. FIG. 13B discloses SEQ ID NOS 42-46, 48, 47 and 49, respectively, in order of appearance.

FIG. 15A depicts a primary screen identifying hit sequences targeting ApoE in HepG2 cells. FIG. 15B illustrates the effectiveness and potency of hit sequences from the primary screen in HepG2 cells. FIG. 15C depicts dose response curves of hit sequences from the primary screen in HepG2 cells.

FIG. 17D includes graphs showing that the simultaneous injection of Di-siRNA$^{ApoE1156}$ and agonist compounds blocked liver silencing without impacting silencing in the brain.

DETAILED DESCRIPTION

Figure 1A:
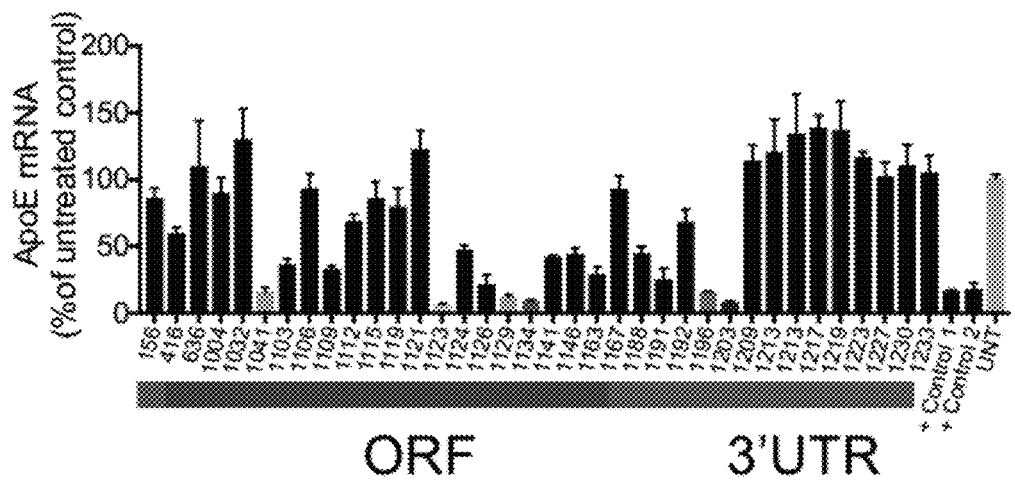
FIGS. 1A-1C illustrate the identification of novel targeting sequences showing silencing in both mRNA and protein based mouse cell models.

Novel combination of an RNA silencing agent for silencing a target mRNA in one or more target tissues with a repressor of the RNA silencing agent to inhibit silencing of the target mRNA in one or more off-target tissues are provided. The disclosure also provides novel methods for treating and preventing diseases by silencing a target mRNA in a target tissue while inhibiting target mRNA silencing in off-target tissues.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In one embodiment, a siRNA comprises between about 15-30 nucleotides or nucleotide analogs, in another embodiment between about 16-25 nucleotides (or nucleotide analogs), in yet another embodiment between about 18-23 nucleotides (or nucleotide analogs), and in another embodiment between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide, which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions, which allow the nucleotide to perform its intended function, such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. In one embodiment, RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA, which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules, which are substantially free of other cellular material or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules, which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location, which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) and causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals who share at least one common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of consecutive glutamine residues linked to peptide bonds. In one embodiment the consecutive region includes at least 5 glutamine residues (SEQ ID NO: 50).

The term "expanded polyglutamine domain" or "expanded polyglutamine segment," as used herein, refers to a segment or domain of a protein that includes at least 35 consecutive glutamine residues (SEQ ID NO: 51) linked by peptide bonds. Such expanded segments are found in subjects afflicted with a polyglutamine disorder, as described herein, whether or not the subject has manifest symptoms.

The term "trinucleotide repeat" or "trinucleotide repeat region," as used herein, refers to a segment of a nucleic acid sequence e.g., that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE mental retardation, Friedreich's ataxia and myotonic dystrophy. Exemplary trinucleotide repeats diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present disclosure, as there is no suitable mRNA to be targeted by RNAi. By contrast, disease such as Friedreich's ataxia may be suitable for treatment according to the methodologies of the disclosure because, although the causative mutation is not within a coding region (i.e., lies within an intron), the mutation may be within, for example, an mRNA precursor (e.g., a pre-spliced mRNA precursor).

The phrase "examining the function of a gene in a cell or organism" refers to examining or studying the expression, activity, function or phenotype arising therefrom.

As used herein, the term "RNA silencing agent" refers to an RNA, which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small noncoding RNAs can be generated. Exemplary RNA silencing agents include siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to small (10-50 nucleotide) RNA, which are genetically encoded (e.g., by viral, mammalian, or plant genomes) and are capable of directing or mediating RNA silencing. An "miRNA disorder" refers to a disease or disorder characterized by an aberrant expression or activity of an miRNA.

As used herein, the term "dual functional oligonucleotide" refers to a RNA silencing agent having the formula T-L-µ, wherein T is an mRNA targeting moiety, L is a linking moiety, and µ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand, or first strand, has a sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. The miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog, such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety), which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant disclosure include a step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the disclosure are described in further detail in the following subsections.

I. Novel Target Sequences

In certain exemplary embodiments, RNA silencing agents of the disclosure are capable of targeting 5' GUUUAAUAAAGAUUCACCAAGUUUCACGCAAA 3' (SEQ ID NO: 1). In certain exemplary embodiments, RNA silencing agents of the disclosure are capable of targeting one or more of the target sequences 5' GAUUCACCAAGUUUA 3' (SEQ ID NO: 2) and 5' CAAGUUUCACGCAA (SEQ ID NO: 4).

Genomic sequence for each target sequence can be found in, for example, the publicly available database maintained by the NCBI.

II. siRNA Design

In some embodiments, siRNAs are designed as follows. First, a portion of the target gene (e.g., the ApoE gene), e.g., one or more of the target sequences set forth in Table 1, Table 2, or Table 3 is selected. Cleavage of mRNA at these sites should eliminate translation of corresponding protein. Sense strands were designed based on the target sequence. (See FIG. 3A). Preferably the portion (and corresponding sense strand) includes 19 to 25 nucleotides, e.g., 19, 20, 21, 22, 23, 24 or 25 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant disclosure provided that they retain the ability to mediate RNAi. Longer RNAi agents have been demonstrated to elicit an interferon or PKR response in certain mammalian cells which may be undesirable. In embodiments, the RNAi agents of the disclosure do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2-, 3-, 4-, 5-, 6- or 7-nucleotide overhangs are generated, i.e., the 3' end of the sense strand extends 1, 2, 3, 4, 5, 6 or 7 nucleotides further than the 5' end of the antisense strand and/or the 3' end of the antisense strand extends 1, 2, 3, 4, 5, 6 or 7 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this application. In one embodiment, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C: A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the ApoE target sequences set forth at FIGS. 3A-3B is described in detail below. The siRNAs can be designed according to the above exemplary teachings for any other target sequences found in the ApoE gene. Moreover, the technology is applicable to targeting any other target sequences, e.g., non-disease-causing target sequences.

To validate the effectiveness by which siRNAs destroy mRNAs (e.g., ApoE mRNA), the siRNA can be incubated with cDNA (e.g., ApoE cDNA) in a *Drosophila*-based in vitro mRNA expression system. Radiolabeled with $^{32}P$, newly synthesized mRNAs (e.g., ApoE mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

III. RNAi Agents

The present disclosure includes siRNA molecules designed, for example, as described above. The siRNA molecules can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present disclosure include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., ApoE genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding ApoE, targeting the same gene or multiple genes, and can be driven, for example, by separate PolIII promoter sites.

Animal cells express a range of noncoding RNAs of approximately 22 nucleotides termed micro RNA (miR-NAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by a "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the disclosure include both unmodified siRNAs and modified siRNAs as known in the art, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the disclosure can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present disclosure can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-ApoE RNA Silencing Agents

In one embodiment, the present disclosure provides novel anti-ApoE RNA silencing agents (e.g., siRNA and shRNAs), methods of making said RNA silencing agents, and methods (e.g., research and/or therapeutic methods) for using said improved RNA silencing agents (or portions thereof) for RNA silencing of ApoE protein. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); and (5) single-stranded, fully phosphorothioated tails of 5-8 bases. The number of phosphorothioate modifications is varied from 6 to 17 in total in different embodiments.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the disclosure having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

Representative compounds of the disclosure can be described in the following aspects and embodiments.

In a first aspect, provided herein is an oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide and a second oligonucleotide, wherein: (1) the first oligonucleotide is an oligonucleotide described herein (e.g., comprising one of the target sequences of FIG. 3A); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In a third aspect, provided herein is an oligonucleotide having the structure:

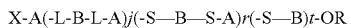

wherein: X is a 5' phosphate group; A, for each occurrence, independently is a 2'-methoxy-ribonucleotide; B, for each occurrence, independently is a 2'-fluoro-ribonucleotide; L, for each occurrence independently is a phosphodiester or phosphorothioate linker; S is a phosphorothioate linker; and R is selected from hydrogen and a capping group (e.g., an acyl such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein: (1) the first oligonucleotide is selected from the oligonucleotides of the third aspect; (2) a portion of the first oligonucleotide is complementary to a portion of the second oligonucleotide; and (3) the second oligonucleotide has the structure:

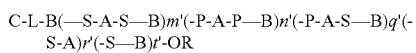

wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-4 repeat units of ethyleneglycol, a phosphodiester, and a phosphorothioate; S is a phosphorothioate linker; P is a phosphodiester linker; R is selected from hydrogen and a capping group (e.g., an acyl such as acetyl); m' is 0 or 1; n' is 4, 5 or 6; q' is 0 or 1; r' is 0 or 1; and t' is 0 or 1.

a) Design of Anti-ApoE siRNA Molecules

An siRNA molecule of the disclosure is a duplex including a sense strand and complementary antisense strand, the antisense strand having sufficient complementary to an ApoE mRNA to mediate RNAi. In one embodiment, the siRNA molecule has a length from about 10-50 or more nucleotides, i.e., each strand comprises 10-50 nucleotides (or nucleotide analogs). In another embodiment, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one embodiment, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In another embodiment, the siRNA molecule has a length from about 10-50 or more nucleotides, i.e., each strand comprises 10-50 nucleotides (or nucleotide analogs). In yet another embodiment, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Usually, siRNAs can be designed by using any method known in the art, for instance, by using the following protocol:

1. The siRNA should be specific for a target sequence, e.g., a target sequence set forth in FIG. 3A. In one embodiment, a target sequence is found in a wild-type ApoE allele. In another embodiment, a target sequence is found in both a mutant ApoE allele, and a wild-type ApoE allele. In another embodiment, a target sequence is found in a wild-type ApoE allele. The first strand should be complementary to the target sequence, and the other strand is substantially complementary to the first strand. (See FIGS. 3A-3B for exemplary sense and antisense strands.) Exemplary target sequences are selected from the 5' untranslated region (5'-UTR) of a target gene. Cleavage of mRNA at these sites should eliminate translation of corresponding ApoE protein. Target sequences from other regions of the ApoE gene are also suitable for targeting. A sense strand is designed based on the target sequence. Further, siRNAs with lower G/C content (35-55%) may be more active than those with G/C content higher than 55%. Thus, in one embodiment, the nucleic acid molecules can have 35-55% G/C content.

2. The sense strand of the siRNA is designed based on the sequence of the selected target site. In one embodiment, the sense strand includes about 19 to 25 nucleotides, e.g., 19, 20, 21, 22, 23, 24 or 25 nucleotides. In another embodiment, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention, provided that they retain the ability to mediate RNAi. Longer RNA silencing agents have been demonstrated to elicit an interferon or Protein Kinase R (PKR) response in certain mammalian cells which may be undesirable. In yet another embodiment the RNA silencing agents of the disclosure do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention disclosure have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a one embodiment, the sense strand of the siRNA is designed to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The embodiments herein have the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant: wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(#of A+T bases)+4(#of G-C bases). For hybrids between 18 and 49 base pairs in length, Tm(° C.)=81.5+16.6(log 10[Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant ApoE mRNA), the siRNA may be incubated with target cDNA (e.g., ApoE cDNA) in a Drosophila-based in vitro mRNA expression system. Radiolabeled with $^{32}$P, newly synthesized target mRNAs (e.g., ApoE mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-ApoE siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth at FIG. 3A, and an antisense strand comprising a sequence set forth at FIG. 3A.

Sites of siRNA-mRNA complementation are selected which result in optimal mRNA specificity and maximal mRNA cleavage.

b) siRNA-Like Molecules siRNA-like molecules of the disclosure have a sequence (i.e., have a strand having a sequence) that is "sufficiently complementary" to a target sequence of an ApoE mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an ApoE target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. The shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the ApoE target sequence. In one embodiment, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In some embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the disclosure include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., ApoE mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the disclosure include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thaliana, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). The miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present application include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding an miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present application can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the application are designed such that they recruit miRNAs (e.g., endogenous cellular miRNAs) to a target mRNA so as to induce the modulation of a gene of interest. In some embodiments, the tethers have the formula T-L-µ, wherein T is an mRNA targeting moiety, L is a linking moiety, and µ is an miRNA recruiting moiety. Any one or more moiety may be double stranded. In some embodiment, however, each moiety is single stranded.

Moieties within the tethers can be arranged or linked (in the 5' to 3' direction) as depicted in the formula T-L-µ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the application, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the disclosure, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., ApoE gene expression) can be modulated using oligonucleotide-based compounds comprising two or more single stranded antisense oligonucleotides that are linked through their 5'-ends that allow the presence of two or more accessible 3'-ends to effectively inhibit or decrease ApoE gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the disclosure, therefore, comprise two or more oligonucleotides linked to a nucleotide or a non-nucleotide linker. Such oligonucleotides according to the disclosure are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

V. Modified RNA Silencing Agents

In certain aspects of the disclosure, an RNA silencing agent (or any portion thereof) as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In some embodiments, the RNA silencing agents of the disclosure are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is one embodiment because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In some embodiments, the universal nucleotide is an inosine residue or a naturally occurring analog thereof.

In certain embodiments, the RNA silencing agents are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the application may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the application or an siRNA produced from a shRNA) into RISC in favor of the sense strand, such that the antisense strand preferentially guides cleavage or translational repression of a target mRNA, and thus increasing or improving the efficiency of target cleavage and silencing. In one embodiment, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In one embodiment, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). In one embodiment, the base pair is selected from the group consisting of an I:A, I:U and I:C. In yet another embodiment, the asymmetry of an RNA silencing agent of the invention may be enhanced such that there is at least one base pair comprising a modified nucleotide. In some embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present disclosure can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the disclosure features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the application features RNA silencing agents that are at least 80% chemically modified. In a one embodiment of the present invention, the RNA silencing agents may be fully chemically modified, i.e., 100% of the nucleotides are chemically modified.

In a one embodiment, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. In one embodiment, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Some modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribothymidine, 2-aminopurine, 2'-aminobutyryl-pyrene-uridine, 5-fluoro-cytidine, and 5-fluoro-uridine. 2'-deoxy-nucleotides and 2'-OMe nucleotides can also be used within modified RNA-silencing agents moities of the instant disclosure. Additional modified residues include, deoxy-abasic, inosine, N3-methyl-uridine, N6,N6-dimethyladenosine, pseudouridine, purine ribonucleoside and ribavirin. In a one embodiment, the 2' moiety is a methyl group such that the linking moiety is a 2'-O-methyl oligonucleotide.

In an exemplary embodiment, the RNA silencing agent of the disclosure comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the disclosure comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also some embodiments are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the disclosure includes RNA silencing agents having two complementary strands of nucleic acid, wherein the two strands are crosslinked. The application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' OMe moiety and modification of the backbone, e.g., with the replacement of a 0 with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the disclosure includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Sunni. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of disclosure is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the disclosure. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or Eu(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to an RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine (GalNac), N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a one embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. In one embodiment, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is, in one embodiment, an alpha-helical agent, which has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

In a certain embodiment, the targeting agent is a hydrophobic moiety. In a certain embodiment, the hydrophobic moiety is selected from the group consisting of fatty acids, steroids, secosteroids, lipids, gangliosides and nucleoside analogs, endocannabinoids, and vitamins. In a certain embodiment, the steroid selected from the group consisting of cholesterol and Lithocholic acid (LCA). In a certain embodiment, the fatty acid selected from the group consisting of Eicosapentaenoic acid (EPA), Docosahexaenoic acid (DHA) and Docosanoic acid (DCA). In a certain embodiment, the vitamin selected from the group consisting of choline, vitamin A, vitamin E, and derivatives or metabolites thereof. In a certain embodiment, the vitamin is selected from the group consisting of retinoic acid and alpha-tocopheryl succinate.

6) Branched Oligonucleotides

In other embodiments, RNA silencing agents may be connected to one another by one or more moieties independently selected from a linker, a spacer and a branching point. The branched RNA silencing agents may thus form branched oligonucleotides having two to eight oligonucleotides attached through a linker. The linker may be hydrophobic. In an exemplary embodiment, the branched oligonucleotides include two or three oligonucleotides. In an embodiment, the oligonucleotides independently have substantial chemical stabilization (e.g., at least 40% of the constituent bases are chemically-modified). In a further embodiment, the oligonucleotides have full chemical stabilization (i.e., all of the constituent bases are chemically-modified). In some embodiments, compounds of the invention comprise one or more single-stranded phosphorothioated tails, each independently having two to twenty nucleotides. In a particular embodiment, each single-stranded tail has eight to ten nucleotides.

In certain embodiments, compounds of the disclosure are characterized by three properties: (1) a branched structure, (2) full metabolic stabilization, and (3) the presence of a single-stranded tail comprising phosphorothioate linkers. In a particular embodiment, compounds of the invention have 2 or 3 branches. The increased overall size of the branched structures promote increased uptake. Also, without being bound by a particular theory of activity, multiple adjacent branches (e.g., 2 or 3) allow each branch to act cooperatively and thus dramatically enhance rates of internalization, trafficking and release.

In certain embodiments, compounds of the disclosure are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phosphorothioated single oligonucleotides containing at least 3, optimally 5-20 phosphorothioated bonds.

VI. Methods of Introducing Nucleic Acids, Vectors and Host Cells

RNA silencing agents of the disclosure may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the disclosure can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the disclosure (e.g., an siRNA targeting an ApoE target sequence) is tested for its ability to specifically degrade mutant mRNA (e.g., ApoE mRNA and/or the production of ApoE protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant ApoE cDNA). Standard siRNA, modified siRNA or vectors able to produce siRNA from U-looped mRNA are co-transfected. Selective reduction in target mRNA (e.g., ApoE mRNA) and/or target protein (e.g., ApoE protein) is measured. Reduction of target mRNA or protein can be compared to levels of target mRNA or protein in the absence of an RNAi agent or in the presence of an RNAi agent that does not target ApoE mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3'

AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VII. Methods of Treatment

The present disclosure provides for both prophylactic and therapeutic methods of treating a subject at risk of (or susceptible to) a disease or disorder caused, in whole or in part, by abnormalities in cholesterol transport. In one embodiment, the disease or disorder is such that ApoE levels in the central nervous system (CNS) have been found to be predictive of neurodegeneration progression. In another embodiment, the disease or disorder is a polyglutamine disorder. In a preferred embodiment, the disease or disorder one in which reduction of ApoE in the CNS reduces clinical manifestations seen in neurodegenerative diseases such as AD and ALS.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the disclosure provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the disclosure pertains to methods treating subjects therapeutically, i.e., alter onset of symptoms of the disease or disorder. In an exemplary embodiment, the modulatory method of the disclosure involves contacting a CNS cell expressing ApoE with a therapeutic agent (e.g., a RNAi agent or vector or transgene encoding same) that is specific for a target sequence within the gene (e.g., SEQ ID NOs:1, 2 or 3), such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the disclosure provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the disclosure can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesias in Parkinson's disease patients. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Some dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. The dosage can be an amount effective to treat or prevent a neurodegenerative disease or disorder, e.g., AD or ALS. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are administered no more than once every 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the disclosure is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is affected or a diminution of disease state is achieved. Optimal dosing schedules can be calculated from measurements of drug accumulation in the body of the patient. Persons of ordinary skill can determine optimum dosages, dosing methodologies and repetition rates. Optimum dosages may vary depending on the relative potency of individual compounds, and can generally be estimated based on $EC_{50}$s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

VIII. Pharmaceutical Compositions and Methods of Administration

The disclosure pertains to uses of the above-described agents for prophylactic and/or therapeutic treatments as described infra. Accordingly, the modulators (e.g., RNAi agents) of the present disclosure can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated and used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is possible to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 µg to 1000 mg may be administered; in some embodiments, 10, 30, 100 or 1000 µg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments.

The nucleic acid molecules of the disclosure can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), supra.

In certain exemplary embodiments, a composition that includes an RNA silencing agent of the disclosure can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. One route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-ApoE RNA silencing agent directly into the brain (e.g., into the globus pallidus or the corpus striatum of the basal ganglia, and near the medium spiny neurons of the corpus striatum). In addition to an RNA silencing agent of the disclosure, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is affected by a conduit leading from the pump or reservoir to the site of release. Devices for delivery to the brain are described, for example, in U.S. Pat. Nos. 6,093,180, and 5,814,014.

An RNA silencing agent of the disclosure can be further modified such that it is capable of traversing the blood brain barrier (BBB). For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; E1-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; E L Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; E1 Andaloussi S, Lakhal S, Mäger I, Wood MJ. (2013). Exosomes for targeted siRNA delivery across biological barriers. Adv Drug Deliv Rev. 2013 March; 65(3):391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((E1-Andaloussi (2012)). By loosening the tight junctions, normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the disclosure can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the disclosure can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the disclosure can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. One group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the disclosure can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

IX. Organ-Selective Gene Modulation

In a further aspect, the present application provides for organ-selective (e.g., tissue-selective) modulation of gene expression by administering an RNA silencing agent (e.g., siRNA, ASO) in combination with an antagonist of the RNA silencing agent, where the antagonist is targeted to specific organs and tissues (e.g., clearance tissues such as the liver, kidney, and spleen).

As used herein, an "antagonist of the RNA silencing agent" or "anti-RNA silencing agent" or "anti-siRNA" or "anti-antisense oligonucleotide" (anti-ASO) is a oligonucleotide (e.g., single-stranded oligonucleotide) with sufficient complementarity to the RNA silencing agent to inhibit, reduce, or eliminate the activity of the RNA silencing agent. In some embodiments, the anti-RNA silencing agent inhibits the silencing (e.g., target RNA cleavage) activity of the RNA silencing agent.

In an embodiment, the anti-RNA silencing agent comprises an oligonucleotide (e.g., single-stranded oligonucleotide) complementary to the guide strand of a target siRNA. In an embodiment, the anti-RNA silencing agent comprises one or more locked nucleic acids. In an embodiment, the anti-RNA silencing agent comprises one or more 2'-methoxy nucleotide modifications. In an embodiment, the anti-RNA silencing agent comprises one or more phosphorothioate linkages. In an embodiment, all internucleotide linkages in the anti-RNA silencing agent comprises phosphorothioate linkages.

In an embodiment, the anti-RNA silencing agent comprises 8 to 20 bases in length. In an embodiment, the anti-RNA silencing agent comprises 8 bases in length. In an embodiment, the anti-RNA silencing agent comprises 9 bases in length. In an embodiment, the anti-RNA silencing agent comprises 10 bases in length. In an embodiment, the anti-RNA silencing agent comprises 11 bases in length. In an embodiment, the anti-RNA silencing agent comprises 12 bases in length. In an embodiment, the anti-RNA silencing agent comprises 13 bases in length. In an embodiment, the anti-RNA silencing agent comprises 14 bases in length. In an embodiment, the anti-RNA silencing agent comprises 15 bases in length. In an embodiment, the anti-RNA silencing agent comprises 16 bases in length. In an embodiment, the anti-RNA silencing agent comprises 17 bases in length. In an embodiment, the anti-RNA silencing agent comprises 18 bases in length. In an embodiment, the anti-RNA silencing agent comprises 19 bases in length. In an embodiment, the anti-RNA silencing agent comprises 20 bases in length.

In an embodiment, the anti-RNA silencing agent comprises 5' (mN)#(lN)#(mN)#(mN)#(mN)#(mN)#(lN)#(mN)#(lN)#(lN)#(mN)#(lN)#(lN)#(mN)(N) 3'

In an embodiment, the anti-RNA silencing agent comprises 5' (mN)#(lN)#(mN)#(mN)#(mN)#(mN)#(lN)#(mN)#(lN)#(lN)#(mN)#(lN)#(lN)#(mN)(N)-GalNAc 3'.

In an embodiment, the anti-RNA silencing agent comprises 5' (mN)#(lN)#(mN)#(mN)#(mN)#(lN)#(lN)#(mN)#(lN)#(lN)#(lN)#(mN)#(lN)#(mN)(N) 3'

In an embodiment, the anti-RNA silencing agent comprises 5' (mN)#(lN)#(mN)#(mN)#(mN)#(lN)#(lN)#(mN)#(lN)#(lN)#(lN)#(mN)#(lN)#(mN)(N)-GalNAc 3'.

In an embodiment, the anti-RNA silencing agent comprises 5' (mN)#(lN)#(mN)#(mN)#(mN)#(lN)#(mN)#(mN)#(lN)#(lN)#(mN)#(lN)#(lN)#(lN)(N) 3'

In an embodiment, the anti-RNA silencing agent comprises 5' (mN)#(lN)#(mN)#(mN)#(mN)#(lN)#(mN)#(mN)#(lN)#(lN)#(mN)#(lN)#(lN)#(lN)(N)-GalNAc 3'.

In an embodiment, the anti-RNA silencing agent comprises 5' (mN)#(lN)#(mN)#(mN)#(mN)#(mN)#(mN)#(lN)#(lN)#(lN)#(mN)#(lN)#(lN)#(lN)(N) 3'

In an embodiment, the anti-RNA silencing agent comprises 5' (mN)#(lN)#(mN)#(mN)#(mN)#(mN)#(mN)#(lN)#(lN)#(lN)#(mN)#(lN)#(lN)#(lN)(N)-GalNAc 3'.

In an embodiment, the anti-RNA silencing agent comprises 5' (lN)#(mN)#(lN)#(lN)#(mN)#(lN)#(lN)#(mN)(N) 3'

In an embodiment, the anti-RNA silencing agent comprises 5' (lN)#(mN)#(lN)#(lN)#(mN)#(lN)#(lN)#(mN)(N)-GalNAc 3'.

In an embodiment, the anti-RNA silencing agent comprises 5' (lN)#(mN)#(lN)#(lN)#(lN)#(mN)#(lN)#(mN)(N) 3'

In an embodiment, the anti-RNA silencing agent comprises 5' (lN)#(mN)#(lN)#(lN)#(lN)#(mN)#(lN)#(mN)(N)-GalNAc 3'.

In an embodiment, the anti-RNA silencing agent comprises 5' (mN)#(mN)#(lN)#(lN)#(mN)#(lN)#(lN)#(lN)(N) 3'

In an embodiment, the anti-RNA silencing agent comprises 5' (mN)#(mN)#(lN)#(lN)#(mN)#(lN)#(lN)#(lN)(N)-GalNAc 3'.

In an embodiment, the anti-RNA silencing agent comprises 5' (mN)#(lN)#(lN)#(lN)#(mN)#(lN)#(lN)#(lN)(N) 3'

In an embodiment, the anti-RNA silencing agent comprises 5' (mN)#(lN)#(lN)#(lN)#(mN)#(lN)#(lN)#(lN)(N)-GalNAc 3'.

In the above recited embodiments, "mN" represents a 2'-methoxy nucleotide modification, "lN" represents a locked nucleotide, "#" represents a phosphorothioate linkage, "N" represents any nucleotide base (e.g., A, T, G, C, or U), and "GalNAc" represents a GalNAc conjugated targeting agent.

Figure 10A:
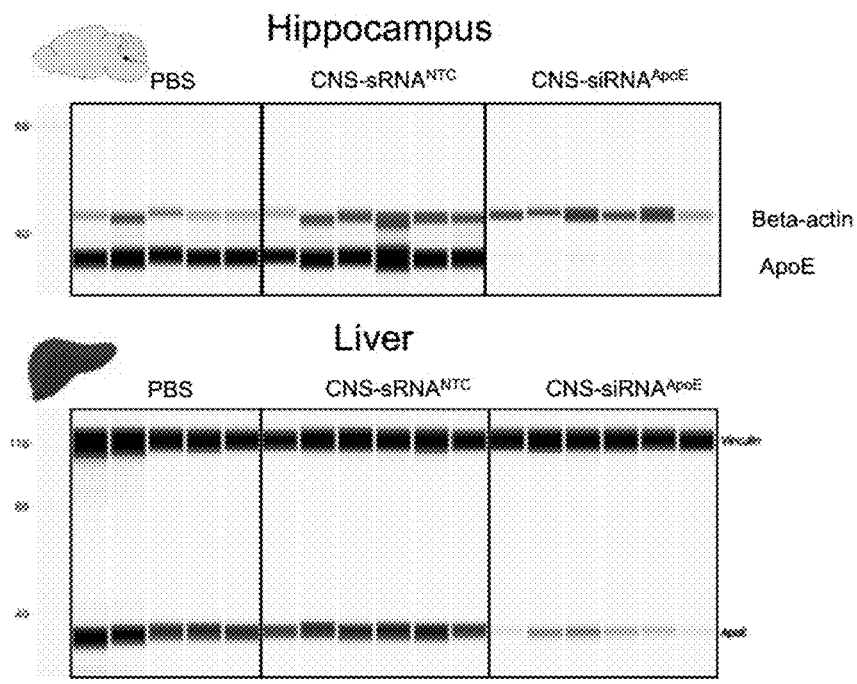
FIGS. 10A-10B show that CNS and systemic ApoE represent two distinct pools of protein.
Figure 10B:
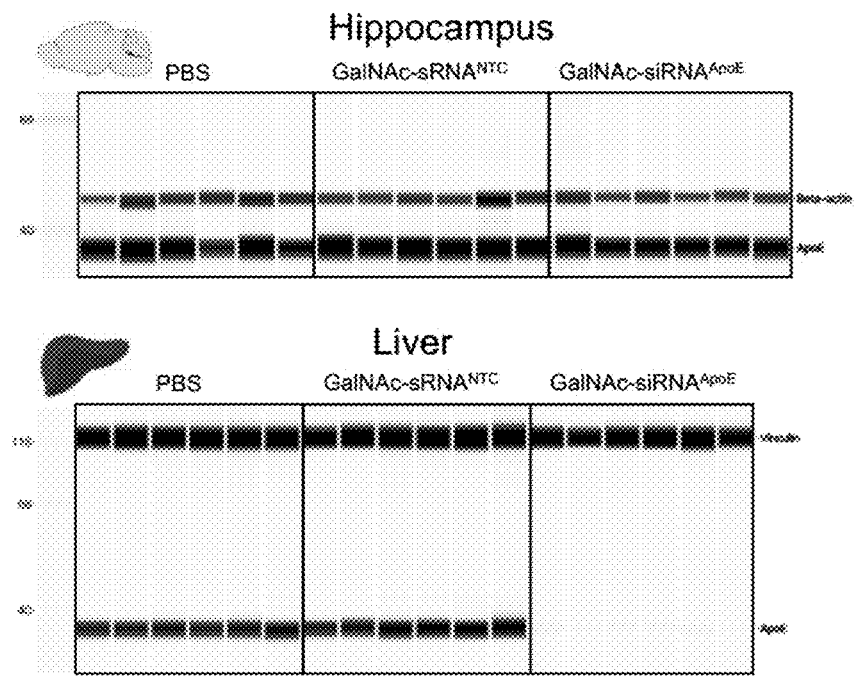
Figure 12:
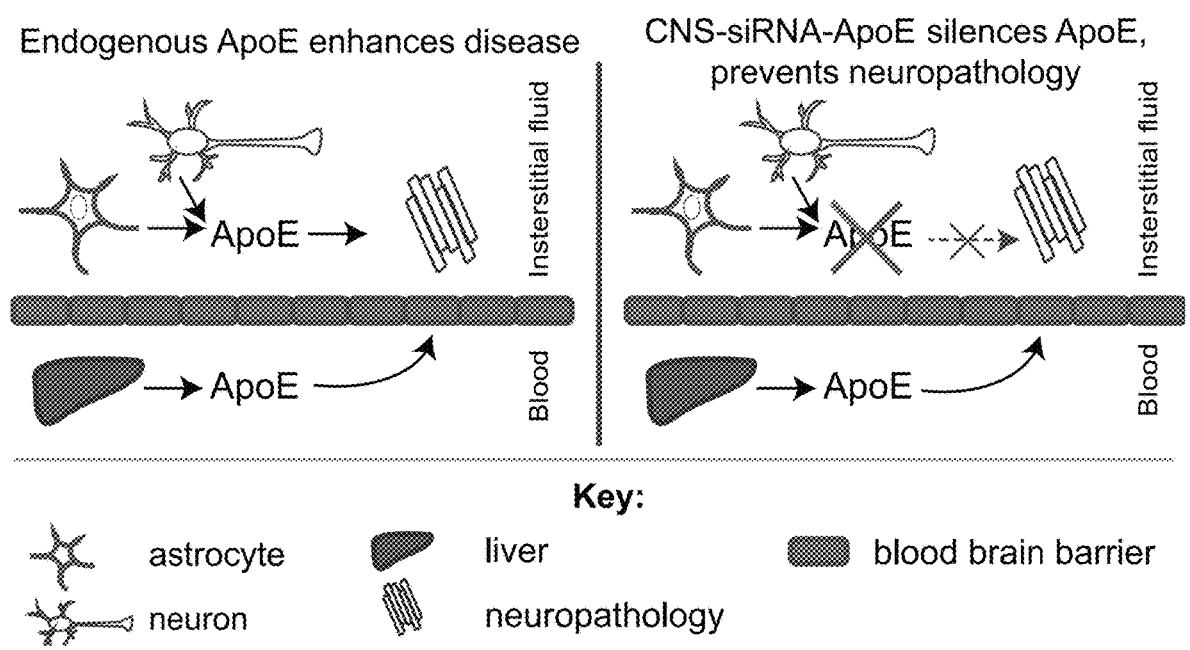
FIG. 12 illustrates the possible involvement of the blood brain barrier in keeping ApoE produced in the liver from reaching the central nervous system (CNS).

It has been discovered in the context of the experiments reported in FIGS. 10A-10B that endogenous ApoE protein produced in the CNS enhances neurodegenerative disease, but ApoE produced in the liver does not. Without being bound by any particular theory, it is believed that the blood brain barrier is impermeable to ApoE, thereby preventing the ApoE produced in the liver or other organs from traversing the barrier to reach the CNS, and vice versa (FIG. 12). The CNS pool of ApoE can thus be modulated in a novel, compartment-specific approach where the silencing of systemic ApoE is blocked.

Combination Therapy

Figure 11A:
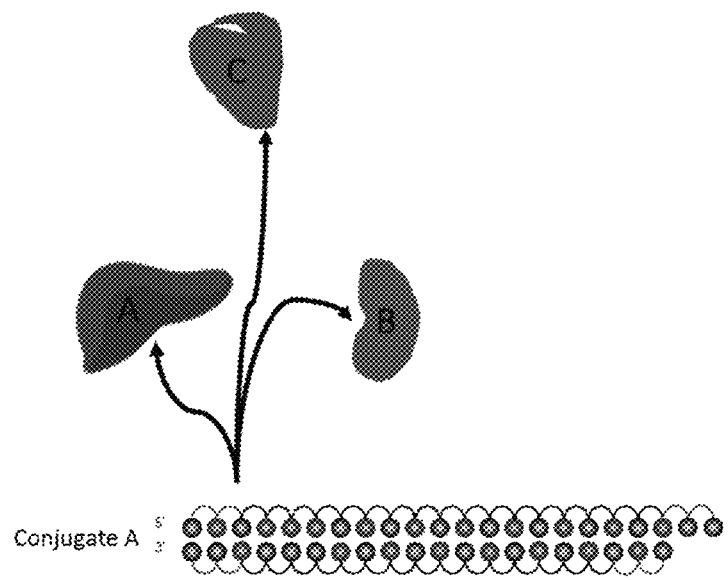
FIGS. 11A-11B illustrate organ-selective modulation of gene expression by administering an RNA silencing agent in combination with an antagonist of the RNA silencing agent, where the antagonist is targeted to specific organs and tissues.
Figure 11B:
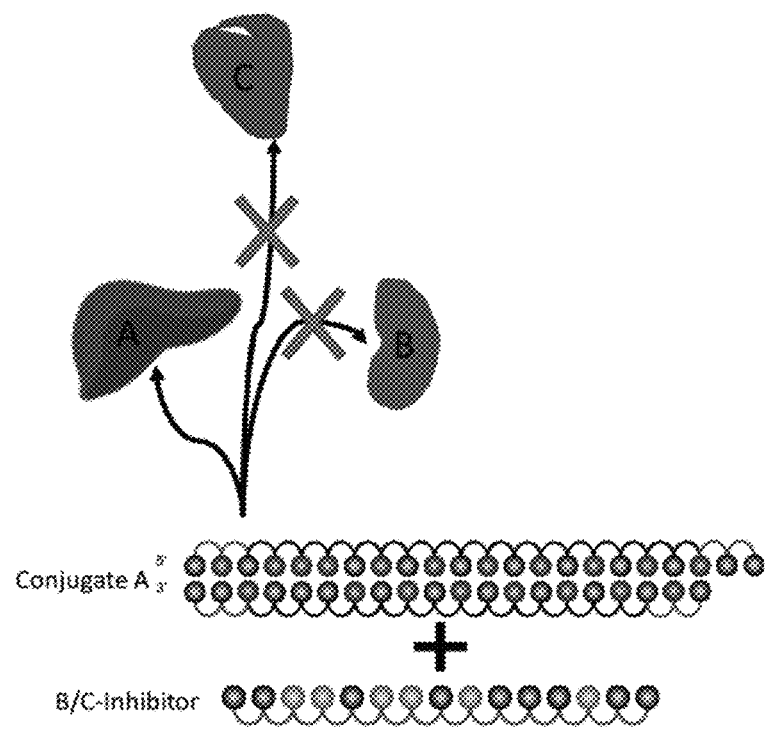

The compartment-specific approach is exemplified in the combination therapy of FIGS. 11A-11B. Combination therapy or polytherapy is the use of more than one medication or other therapy, as opposed to monotherapy, which is any therapy taken alone. An siRNA is administered to a subject as part of a first Conjugate A where the siRNA is bound to a targeting agent that targets to organs A, B, and C. Alternatively, Conjugate A may include a targeting agent directing it to organ A, for example the brain, but a certain percentage ends up in clearance tissues B, C, for instance the kidneys, liver, and spleen. To block unintended silencing of genes in organs B and C, mitigate off target-organ effects, and increase specificity in oligonucleotide therapy, a second conjugate is administered to the subject. In representative embodiments, the second conjugate includes an antagonist to the RNA silencing agent, for example an oligonucleotide featuring a region of complementarity which is substantially complementary to a section of the guide strand of Conjugate A, where the antagonist is conjugated to a targeting agent that is targeted to organs B and C. As a result, and as illustrated in FIG. 11B the first and second conjugates form a selective therapeutic combination specific to organ A and free of undesired off-target activity in organs B and C.

As used herein, the term "off-target tissue" or "off-target organ" refers to any tissue or organ in a subject for which RNA silencing agent activity is not desired. The one or more off-target tissues are not the intended one or more target tissues of the RNA silencing agent. By way of example, but in no way limiting, the target tissue or organ for an RNA silencing agent can be a tissue or organ in the central nervous system (e.g., the brain or spinal cord). An off-target tissue or organ can be one or more of the liver, kidney, or spleen, where the RNA silencing agent can accumulate, but for which RNA silencing agent activity is not desired. Accordingly, the anti-RNA silencing agents of the disclosure will reduce or eliminate RNA silencing agent activity in the off-target tissue or organ.

As used herein, the term "outside the central nervous system" or "non-central nervous system tissue" or "non-central nervous system organ" refers to any tissue or organ that is not a part of the central nervous system. The central nervous system (CNS) includes the brain, spinal cord, and any tissues therein. Non-limiting examples of tissues or organs outside the CNS include the liver, kidney, spleen, lung, muscle, heart, and skin.

As used herein, the term "clearance tissue" or "clearance organ" refers to any tissue or organ that facilitates the removal or clearance of a substance (e.g., an RNA silencing agent) from a subject's plasma. Clearance of a substance can be determined in a variety of art-recognized ways. For example, but in no way limiting, clearance can be a measurement of the volume of plasma from which a substance is completely removed per unit time. This can be represented as L/hour or mL/minute. Non-limiting examples of clearance tissues or organs include the liver, kidney, and spleen.

In representative embodiments, there is provided a therapeutic combination of drugs for the treatment or management of neurodegenerative disease concomitant with a reduction or elimination of unwanted off-target effects. The combination includes a first conjugate and a second conjugate. The first conjugate features an RNA silencing agent and a first targeting agent that targets the first conjugate to the central nervous system. The second conjugate includes an antagonist of the RNA silencing agent and a second targeting agent that targets the second conjugate to a off-target tissue. In certain embodiments, the off-target tissue is a clearance tissue. The first conjugate and second conjugate may be compounded together in a same unitary composition comprising both conjugates. Alternatively, the first conjugate and second conjugate may be formulated as separate pharmaceutical formulations, for example in two separate containers that are provided as components of a kit.

In certain embodiments, the RNA silencing agent inhibits the expression of ApoE in an organism such as a human subject. As such, it can be chosen from among the novel anti-ApoE RNA silencing agents provided in the present application, and may be a single stranded (ss) or double stranded (ds) RNA molecule that is between 15 and 35 bases in length and that includes a region of complementarity which is substantially complementary to one of the sequences of Table 2, wherein the RNA molecule targets an open reading frame (ORF) or 3' untranslated region (UTR) of ApoE gene mRNA. In an embodiment, the region of complementarity is substantially complementary to one or more of 5' GAUUCACCAAGUUUA 3' (SEQ ID NO: 2) and 5' CAAGUUUCACGCAAA 3' (SEQ ID NO: 3).

The RNA silencing agent may be one of those described in sections II-V supra, e.g. an anti-ApoE siRNAs that may be conjugated to a targeting agent directing it to the central nervous system. Example siRNA constructs targeting the CNS, also known as CNS-siRNA, include Di-siRNAs, where two siRNAs are conjugated to one another via a linker. Also contemplated are compositions of matter including RNA silencing agents conjugated to any suitable molecule that enables an agent to traverse the blood brain barrier, as are exosomes containing RNA silencing agents. In instances where the RNA silencing agent is a CNS-siRNA, the antagonist may be a single stranded oligonucleotide that is complementary to the guide strand of the CNS-siRNA and is conjugated to a cell or tissue targeting agent, e.g. GalNac or an antibody, that binds to a specified cell type outside the CNS, for example a liver cell or a kidney cell.

In an exemplary embodiment of this approach, a CNS-siRNA$^{ApoE}$ is administered to the brain of a subject, for example by intracerebroventricular (ICV) injection. To prevent undesired, off-target silencing, an antagonist of the CNS-siRNA$^{ApoE}$ is also administered to the subject. The antagonist may be a single stranded oligonucleotide complementary to the guide strand of the CNS-siRNA$^{ApoE}$ that is conjugated to GalNac or another targeting agent directing it to the liver. FIG. 13A is a schematic representation of the guide strand of a CNS-siRNA$^{ApoE}$ (top) binding to the antagonist (bottom). The antagonist may contain locked nucleic acid modifications (LNA) that will enhance binding to the guide strand and prevent systemic silencing. FIG. 13B illustrates example sequences of antagonists to CNS-siRNA$^{ApoE}$ targeting the sequences of Table 2. LNA modifications are depicted in red and may be located in any location along the sequence of the antagonist.

The combined use of the first conjugate and the second conjugate may reduce the required dosage for any individual conjugate because the onset and duration of effect of the different conjugates may be complementary. In such combination therapies, the first conjugate may be administered to the subject prior to the second conjugate, concurrently with the second conjugate, or after the second conjugate. In some embodiments, the therapeutic combination refers to using specific combinations (e.g., ratios and/or dosing schedules) of first conjugate and second conjugate. More particularly, the invention provides therapeutic combinations and methods for treating neurodegenerative diseases where the first conjugate and second conjugate are administered in a ratio that is particularly effective from a therapeutic standpoint while preventing off-target gene silencing. In representative embodiments, the ratio, that is, the mass-to-mass ratio of (first conjugate):(second conjugate) is about 50 to 1, 40 to 1, 30 to 1, 25 to 1, 20 to 1, 10 to 1, 5 to 1, 2 to 1, 1 to 2, 1 to 5, 1 to 10, 1 to 20, 1 to 30, 1 to 40, or 1 to 50. In some embodiments, the ratio is, or is at least, about 1, 2, 5, 10, 12, 15, 20, or 50. In some embodiments, the ratio is less than about 5, 10, 15, 20, 30, 40, 50, 60, or 70. Example weight-to-weight ratios are about 1, 2, 5, 8, 10, 15, 20, 25, 30, 40, and 50.

The mass-to-mass ratio of (first conjugate):(second conjugate) can be measured over different periods of time. For example, the mass ratio may be based on the respective amounts of first conjugate and second conjugate administered to the subject in a single day, a single week, 14 days, 21 days, or 28 days. The dose of second conjugate can be set, within a therapeutically effective range, based upon a selected ratio and dose of first conjugate. As discussed above, the ratio can be determined using the amount of first conjugate administered to a subject over a single day, a single week, 14 days, 21 days, or 28 days.

The combination therapy provides for both prophylactic and therapeutic methods whereby a subject at risk of (or susceptible to) a disease or disorder is treated by reducing ApoE in the CNS, as described in section VII supra, but cholesterol homeostasis outside the CNS is not affected. Therefore, in one embodiment, there is provided a method of treating, suppressing, or reducing the severity of a of a neurodegenerative disease in a tissue-specific manner. In exemplary embodiments, the neurodegenerative disease is a disorder cased, in whole or in part, by abnormalities in cholesterol transport, for example amyotrophic lateral disease (ALS) and Alzheimer's disease (AD). In some embodiments, the RNA silencing agent inhibits the expression of Apolipoprotein E (ApoE) gene in the central nervous system and the second conjugate maintains cholesterol homeostasis throughout the rest of the body.

Kits

In certain other embodiments, the disclosure provides kits that include a suitable container containing a first pharmaceutically acceptable composition and a second pharmaceutical composition. The first composition includes a first conjugate comprising an RNA silencing agent and a first targeting agent that targets the first conjugate to the central nervous system, and optionally one or more excipients such as carrier compounds. The second composition includes a second conjugate comprising an antagonist of the RNA silencing agent and a second targeting agent that targets the second conjugate to a tissue outside the central nervous system, and also optionally one or more excipients.

In certain embodiments, the first composition and second composition may be provided in the same container, for example as a mixture containing both compositions. Alternatively, it may be desirable to provide the first and second compositions separately in two or more containers, e.g., one container for an RNA silencing agent conjugate, and at least another for a conjugate of the antagonist. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. In Vitro Identification of Hyper-Functional ApoE Targeting Sequences 1.1 Identification of siRNAs Targeting Mouse ApoE that Cause a Dose-Dependent Decrease in mRNA and Protein The mouse ApoE gene was used as a target for mRNA knockdown. A panel of cholesterol-conjugated siRNAs targeting the mouse ApoE gene was developed and screened in primary mouse astrocytes in vitro compared to untreated control cells. The siRNAs were each tested at a concentration of 1.5 µM and the mRNA was evaluated with the QuantiGene gene expression assay (ThermoFisher, Waltham, MA) at the 72 hours timepoint. FIG. 1A reports the results of the screen.

Figure 1B:
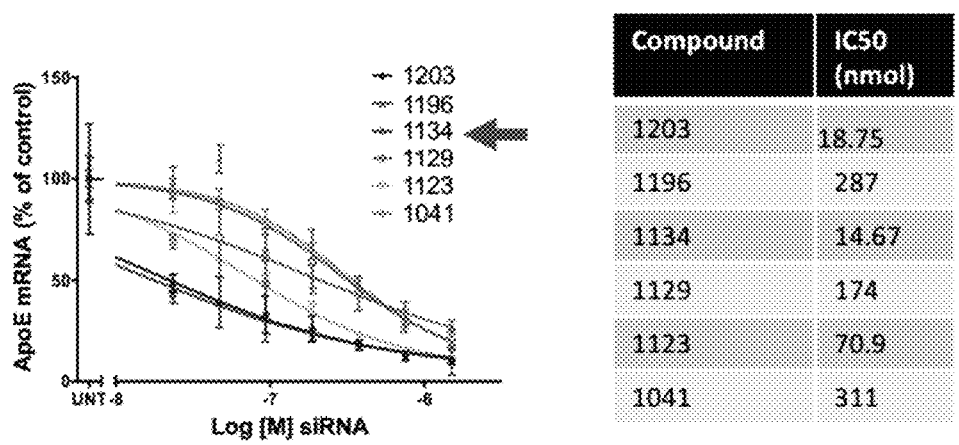
Figure 1C:
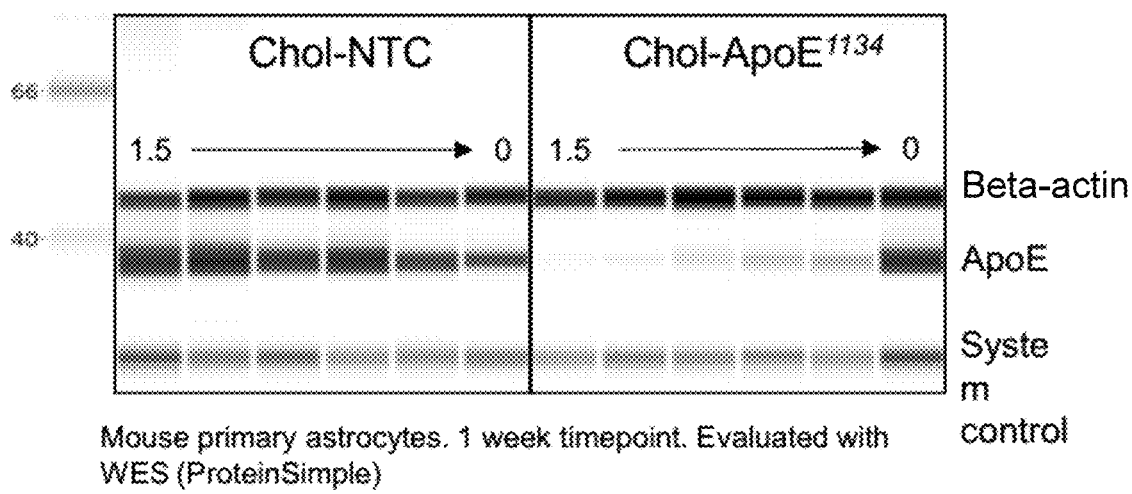

As illustrated in FIG. 1B, dose response curves and IC50 values were obtained for the hit compounds identified in the screen, and 1134 and 1203 were chosen for further studies based on their high efficacy and potency. FIG. 1C illustrates a dose response for 1134 showing protein silencing in mouse primary astrocyte evaluated after 1 week with the Protein-Simple (San Jose, CA) protein quantitation assay. Table 1 below describes the two targets, 1134 and 1203.

TABLE 1

Mouse ApoE mRNA targets, antisense strands, and sense strands.

| ID | Targeting sequence (32 BP) | Antisense sequence (5'-3') | Sense sequence (5'-3') |
|---|---|---|---|
| 1134 | GUUUAAUAAAGAUUCA CCAAGUUUCACGCAAA (SEQ ID NO: 5) | UUGGAUAUGGAU GUUGUUGCAG (SEQ ID NO: 6) | GCAACAACAUC CAUAUCCAA (SEQ ID NO: 7) |
| 1203 | CCUUGCUUAAUAAAGA UUCUCCGAGCACAUU (SEQ ID NO: 8) | UCUCGGAGAAUCU UUAUUAAGC (SEQ ID NO: 9) | UUAAUAAAGAU UCUCCGAGA (SEQ ID NO: 10) |

Figure 2A:
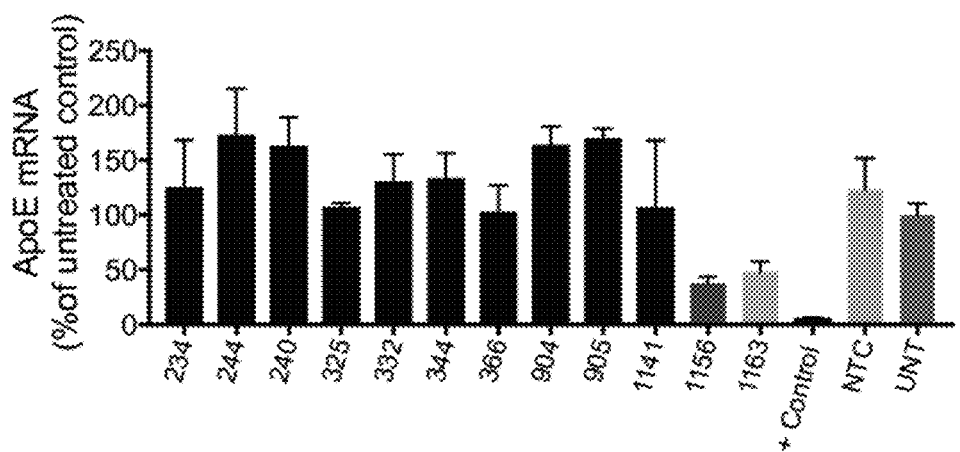
FIGS. 2A-2B illustrate the identification of novel targeting sequences showing mRNA silencing in mRNA based human cell models.
Figure 2B:
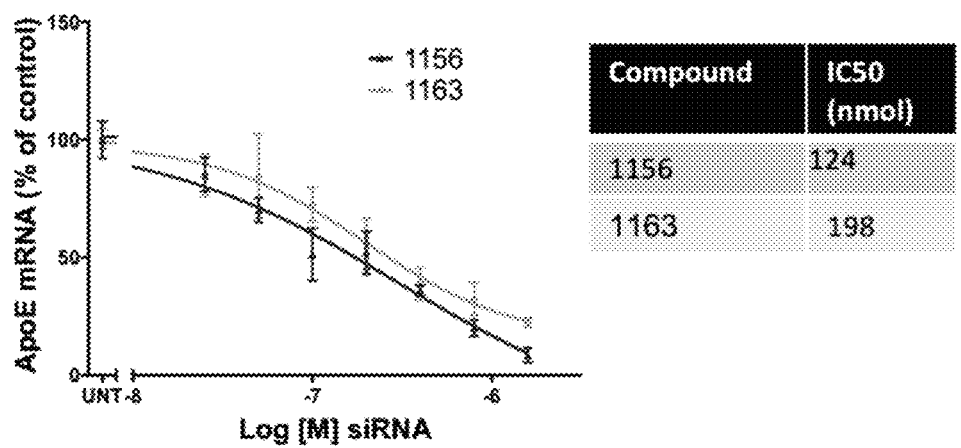

1.2 Identification of siRNAs Targeting Human ApoE that Cause a Dose-Dependent Decrease in mRNA and Protein The human ApoE gene was used as a target for mRNA knockdown. A panel of siRNAs targeting the human ApoE gene was developed and screened in human HepG2 cells in vitro compared to untreated control cells. The siRNAs were each tested at a concentration of 1.5 µM and the mRNA was evaluated with the Quantigene gene expression assay (ThermoFisher, Waltham, MA) at the 72 hours timepoint. FIG. 2A reports the results of the screen and 1156 and 1163 were chosen for further studies based on their high efficacy and potency. Then, and as illustrated in FIG. 2B, dose response curves and IC50 values were obtained for the hit compounds from the screen. Table 2 below describes the two targets, 1156 and 1163.

TABLE 2

Human ApoE mRNA targets, antisense strands, and sense strands.

| ID | Targeting sequence (32 BP) | Antisense sequence (5'-3') | Sense sequence (5'-3') |
|---|---|---|---|
| 1156 | GUUUAAUAAAGAUUCA CCAAGUUUCACGCA (SEQ ID NO: 11) | UAAACUUGGUGA AUCUUUAU (SEQ ID NO: 12) | GAUUCACCAAG UUUA (SEQ ID NO: 48) |
| 1163 | GUUUAAUAAAGAUUCA CCAAGUUUCACGCAAA (SEQ ID NO: 13) | UUUGCGUGAAAC UUGGUGAA (SEQ ID NO: 14) | CAAGUUUCACG CAAA (SEQ ID NO: 49) |

Figure 14:
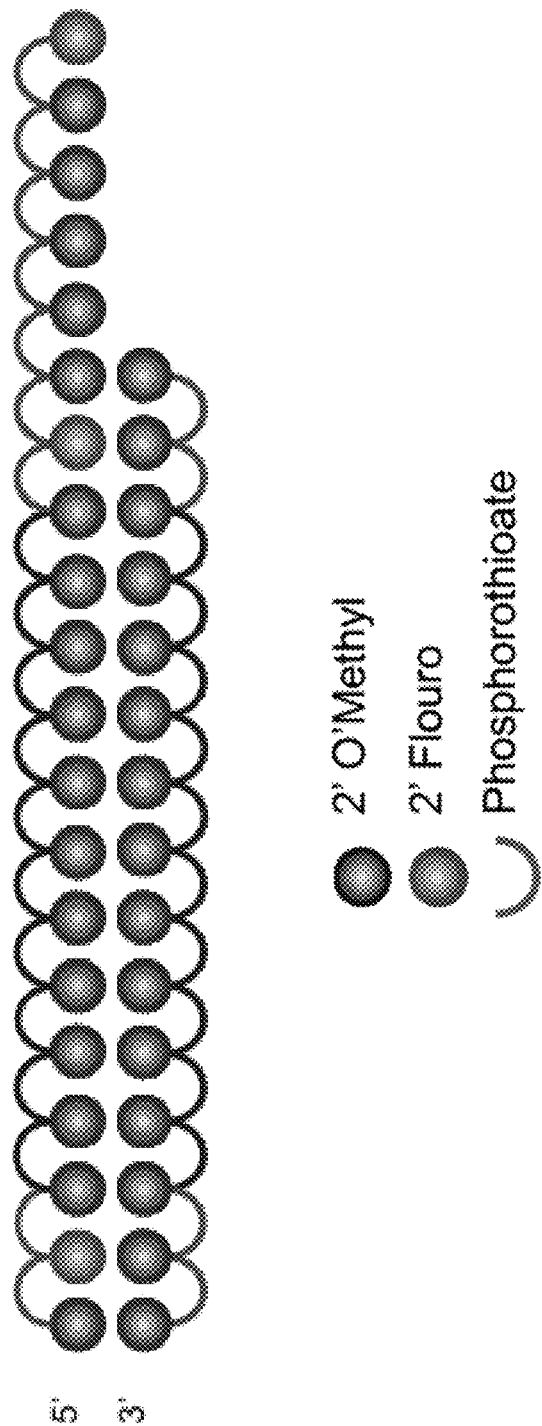
FIG. 14 illustrates an siRNA bearing a methyl-rich substitution pattern.
Figure 15A:
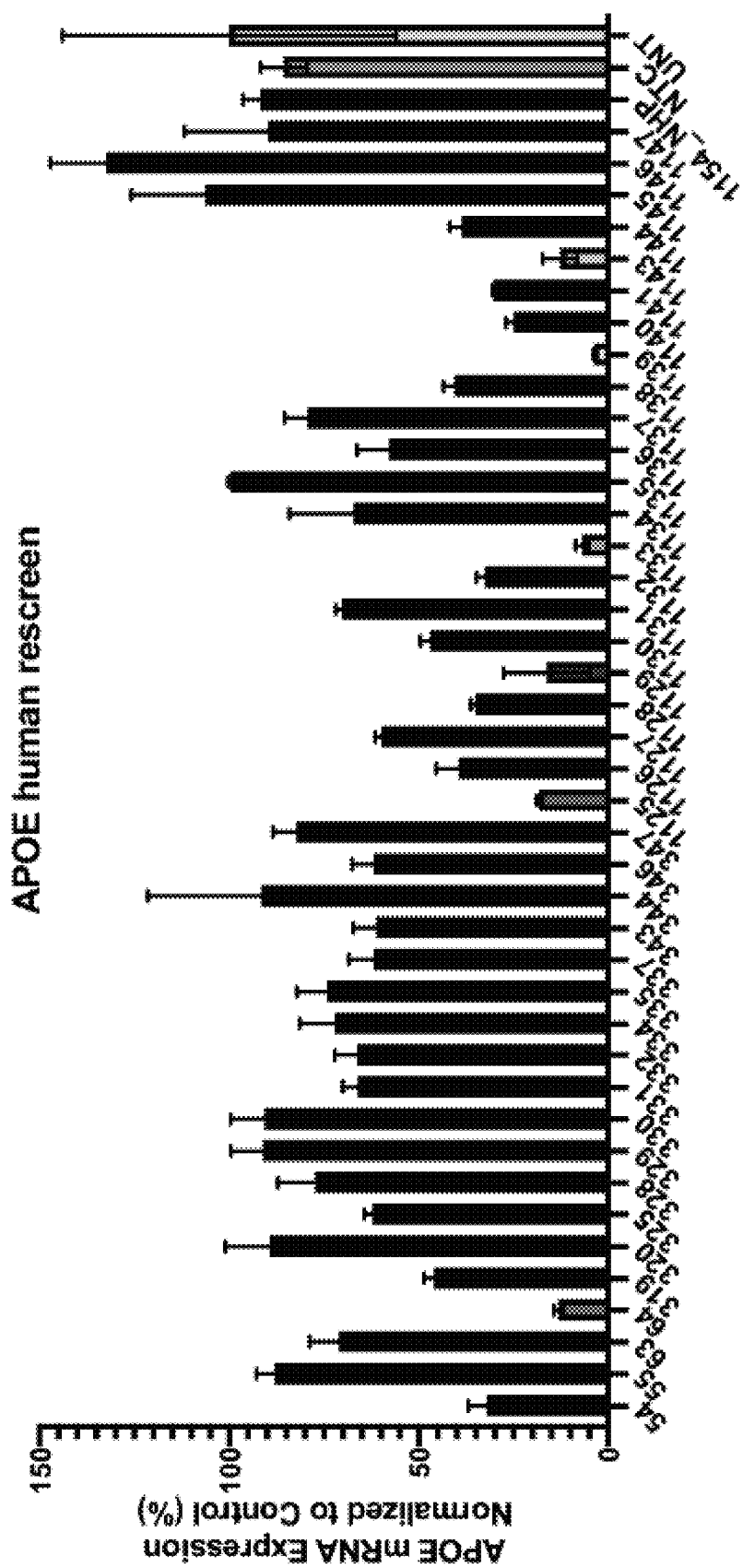
FIGS. 15A-15C illustrate the identification of novel targeting sequences showing mRNA silencing in mRNA based human cell models.
Figure 15B:
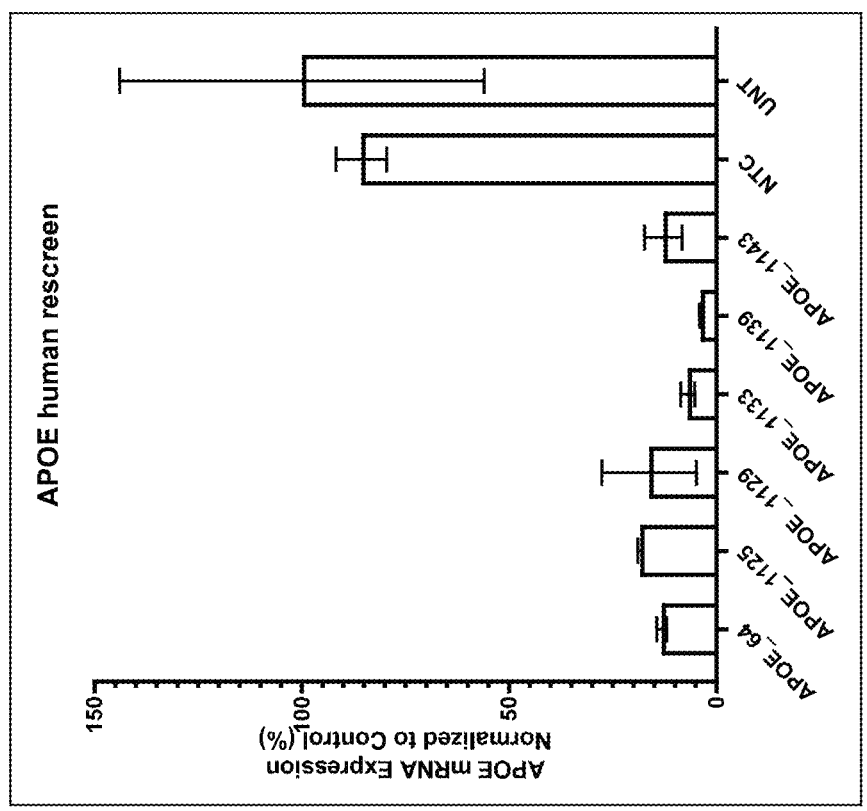
Figure 15C:
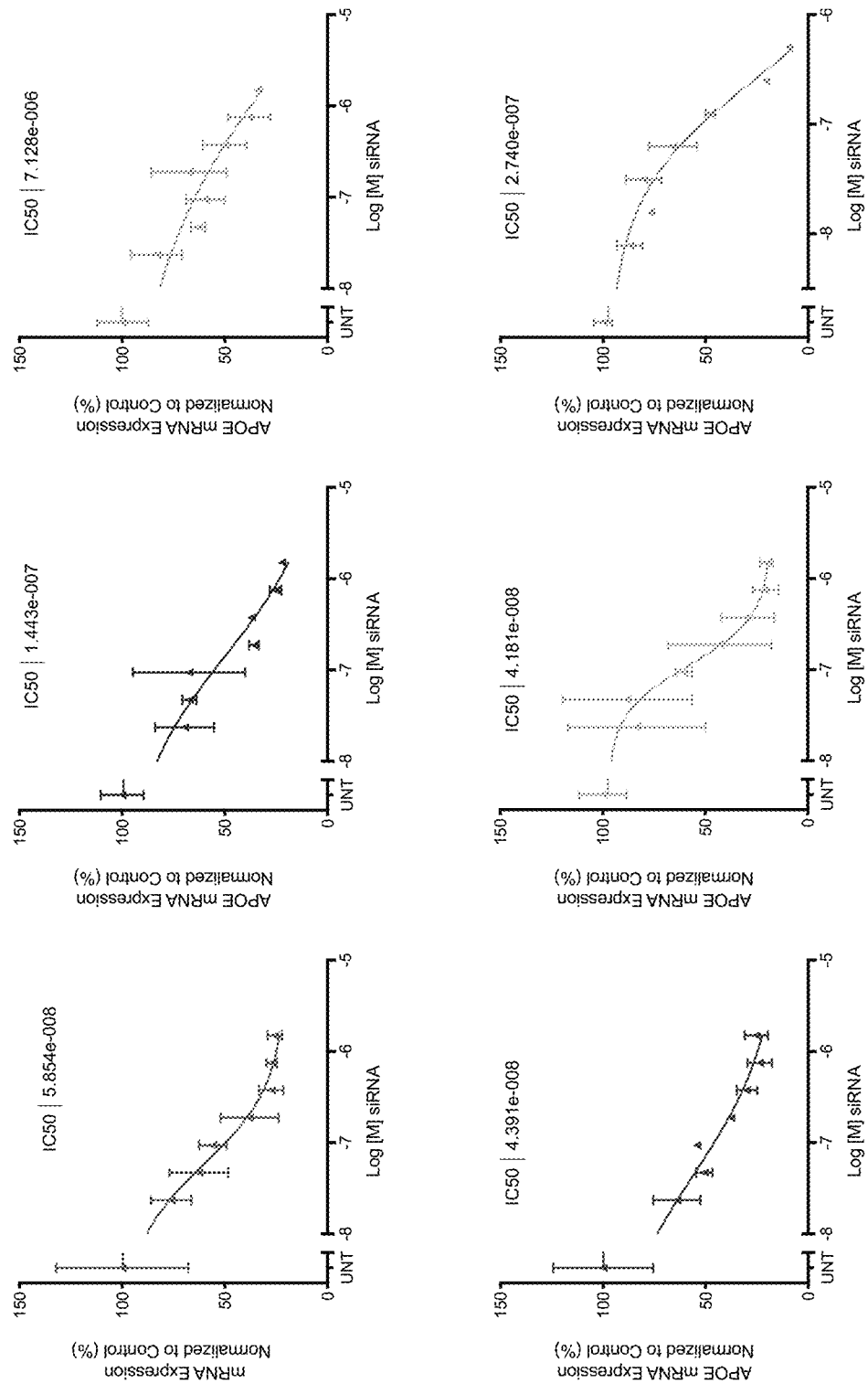

A second screen of the human ApoE gene, this time with siRNAs bearing the methyl-rich chemistry pattern of FIG. 14, was conducted by testing a number of target regions of the gene. FIG. 15A reports the results of the screen and 64, 1125, 1129, 1133, 1139, and 1143 were chosen for further studies based on their high efficacy and potency, as illustrated in FIG. 15B. Then, and as illustrated in FIG. 15C, dose response curves and IC50 values were obtained for the hit compounds from the screen (first row, left to right: 64, 1125, 1129; second row, left to right: 1133, 1139, 1143). Table 3 below describes the target sequences.

It can be seen that the novel siRNA sequences targeting ApoE show potent in vivo mRNA and protein silencing. Previous reports using oligonucleotides to silence ApoE use sequences that demonstrate a ~50% target mRNA and protein silencing after ICV injection. Without being bound to any particular theory, it is possible that many conclusions made using previous sequences are invalid given the low degree of silencing. In contrast, the novel sequences offer a significant advantage in studying the role of ApoE in neurodegeneration.

TABLE 3

Second screen, Human ApoE mRNA targeting regions, targeting sequences, antisense strands, and sense strands.

| ID | Targeting region | Targeting sequence | Sense sequence (5'-3') | Antisense (5'-3') |
|---|---|---|---|---|
| 64 | CAGGCAGGAAGATGAA GGTTCTGTGGGCTG (SEQ ID NO: 15) | AGGAAGAUGAAGG UUCUGUG (SEQ ID NO: 16) | GAUGAAGGUUCUGUG (SEQ ID NO: 17) | CACAGAACCUUC AUCUUCCU (SEQ ID NO: 18) |
| 1125 | TCCTGGGGTGGACCCT AGTTTAATAAAGAT (SEQ ID NO: 19) | GGGUGGACCCUAG UUUAAUA (SEQ ID NO: 20) | GACCCUAGUUUAAUA (SEQ ID NO: 21) | UAUUAAACUAGG GUCCACCC (SEQ ID NO: 22) |
| 1129 | GGGGTGGACCCTAGTT TAATAAAGATTCAC (SEQ ID NO: 23) | GGACCCUAGUUUA AUAAAGA (SEQ ID NO: 24) | CUAGUUUAAUAAAGA (SEQ ID NO: 25) | UCUUUAUUAAAC UAGGGUCC (SEQ ID NO: 26) |
| 1133 | TGGACCCTAGTTTAATA AAGATTCACCAAG (SEQ ID NO: 27) | CCUAGUUUAAUAA AGAUUCA (SEQ ID NO: 28) | UUUAAUAAAGAUUCA (SEQ ID NO: 29) | UGAAUCUUUAUU AAACUAGG (SEQ ID NO: 30) |
| 1139 | CTAGTTTAATAAAGATT CACCAAGTTTCAC (SEQ ID NO: 31) | UUAAUAAAGAUUC ACCAAGU (SEQ ID NO: 32) | AAAGAUUCACCAAGU (SEQ ID NO: 33) | ACUUGGUGAAUC UUUAUUAA (SEQ ID NO: 34) |
| 1143* | GTTTAATAAAGATTCAC CAAGTTTCACGCA (SEQ ID NO: 35) | UAAAGAUUCACCA AGUUUCA (SEQ ID NO: 36) | AUUCACCAAGUUUCA (SEQ ID NO: 37) | UGAAACUUGGUG AAUCUUUA (SEQ ID NO: 38) |

*same targeting region as 1163

1.3 ApoE Targeting Sequences (Mouse and Human)

FIG. 3A is a table illustrating the targeting sequences identified in the mouse and human ApoE genes and antisense and sense sequences of oligonucleotides that target such sequences. As illustrated in FIG. 3B and FIG. 14, the oligonucleotide sequences can be used in the context of a number of chemical modifications (e.g., P2, P3, P2G, P3G) and with different chemical conjugates (e.g., GalNAc, CNS-siRNA, cholesterol). The oligonucleotides can also be used in the context of antisense oligonucleotide gene silencing.

Figure 4A:
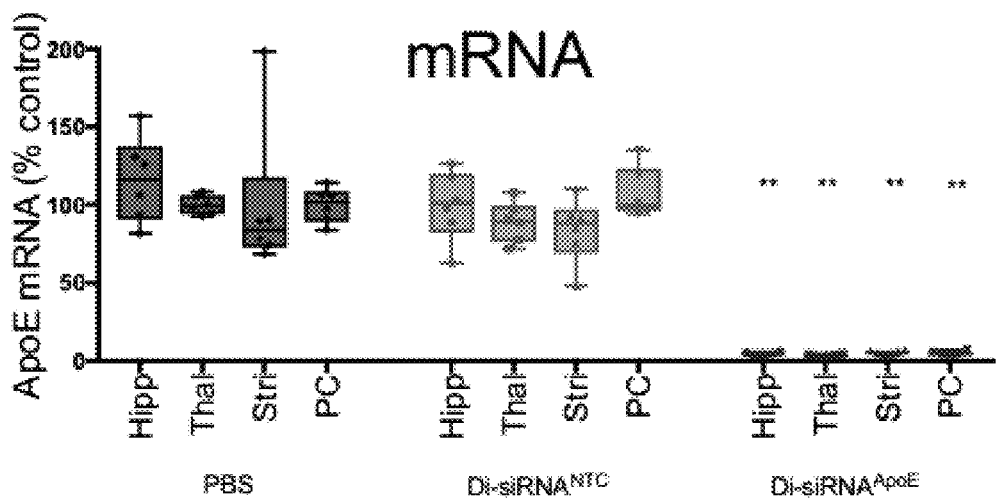
FIGS. 4A-4C illustrate the silencing of mRNA and protein expression throughout the mouse brain 1-month post injection of CNS-siRNA$^{ApoE}$.
Figure 4B:
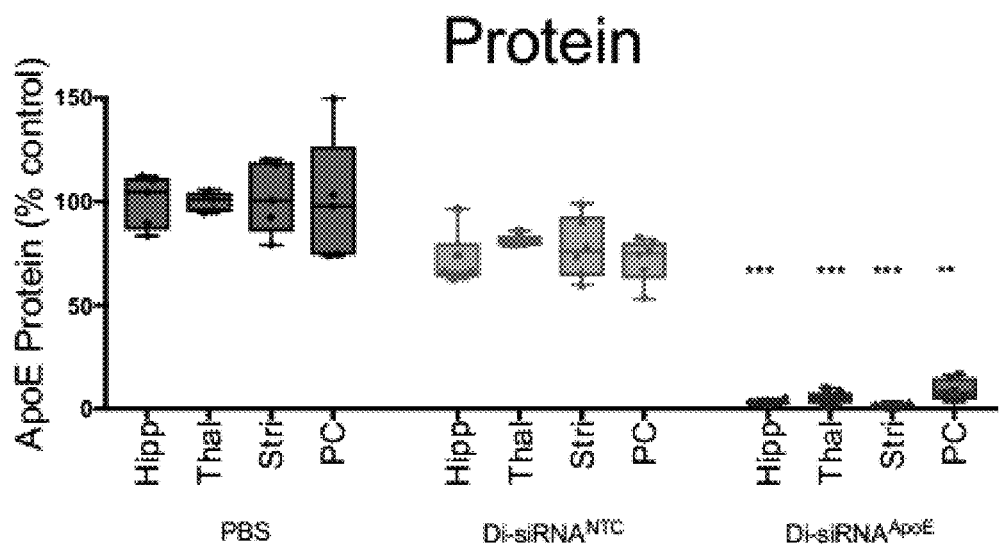
Figure 4C:
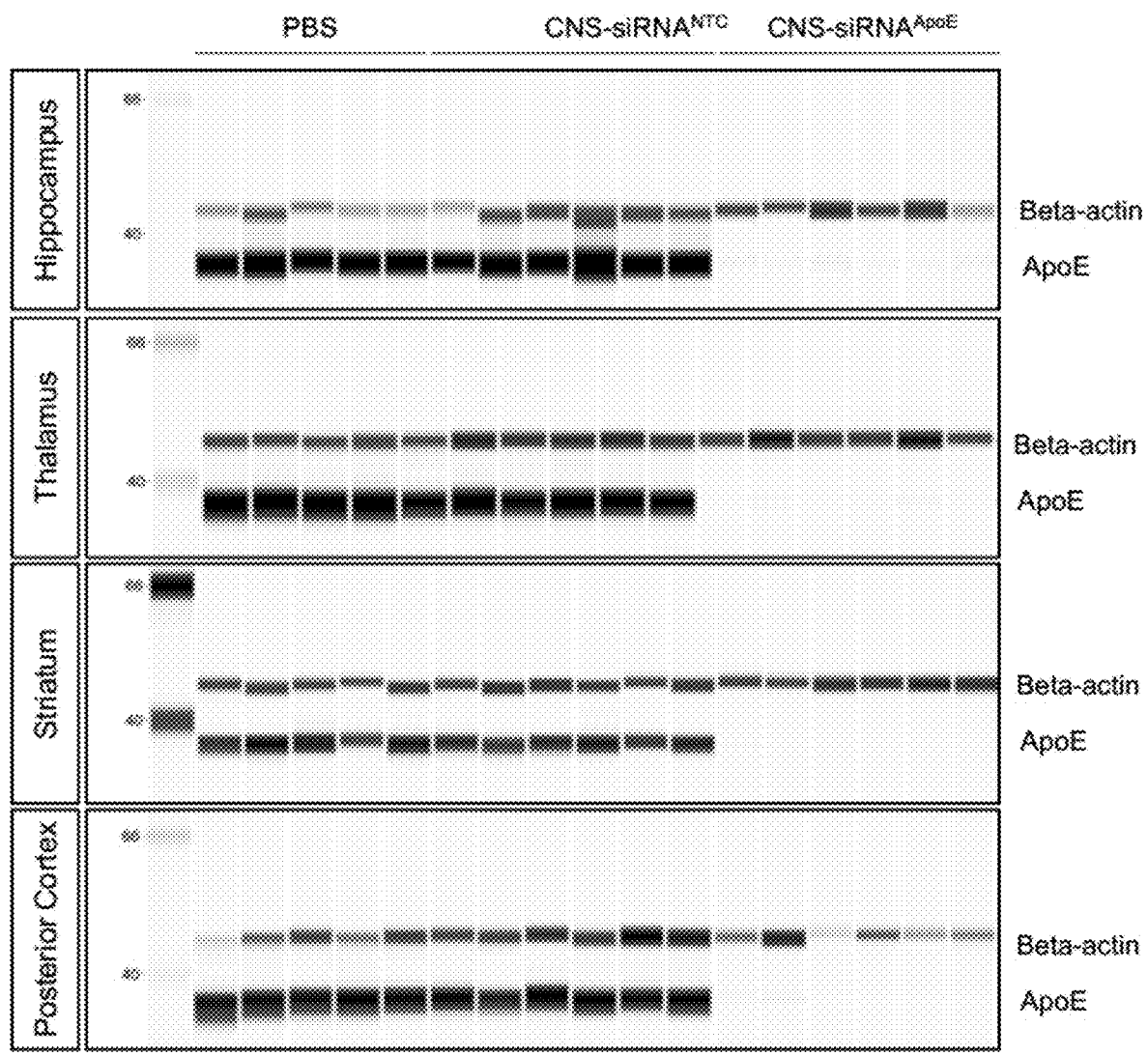

Example 2. In Vivo Efficacy of Tissue-Specific ApoE Targeting siRNAs in Mice 2.1 CNS-siRNA$^{ApoE}$ Silences mRNA and Protein Expression Throughout the Mouse Brain 1-Month Post Injection Di-siRNA$^{ApoE}$ at a dosage of 475 µg was administered via ICV injection to a first group of wild-type mice. A second control group were injected with phosphate-buffered saline (PBS), and a third control group were injected with Di-siRNA$^{NTC}$ (non-targeting control). Each group included six mice. One month after the injection, mRNA silencing was evaluated with QuantiGene in all regions of the brain (FIG. 4A) and protein silencing was evaluated with ProteinSimple (FIG. 4B). Protein silencing throughout the brain was also evaluated with a Western blot (FIG. 4C).

2.2 CNS-siRNA$^{ApoE}$ Silences ApoE Protein in the Hippocampus at Low Doses

Figure 5A:
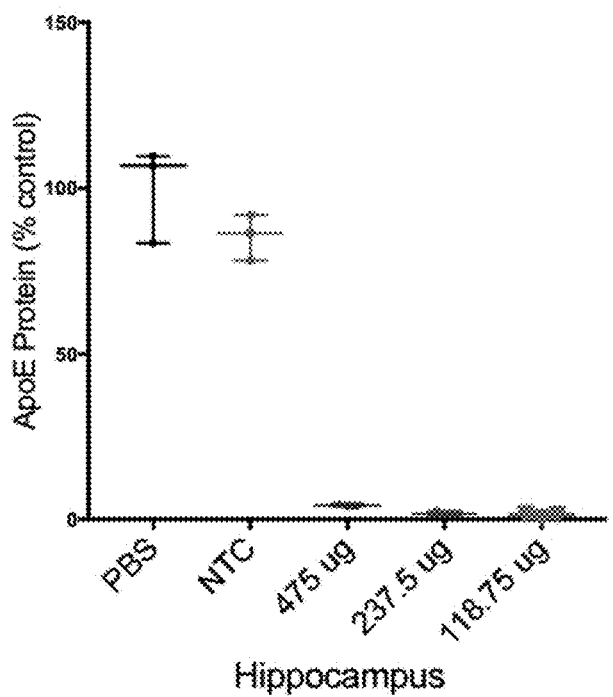
FIGS. 5A-5B show that CNS-siRNA$^{ApoE}$ silences ApoE protein in the hippocampus at low doses.
Figure 5B:
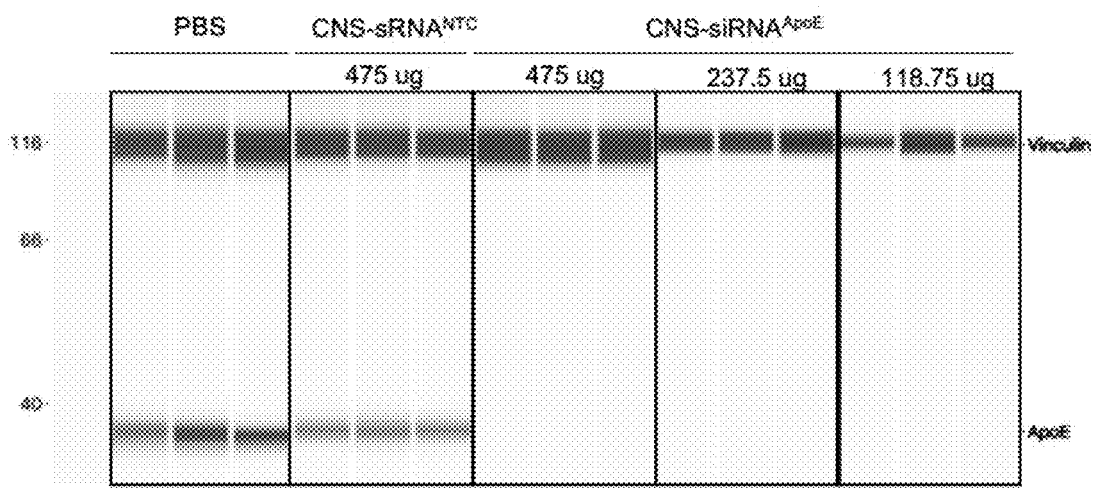

Groups of wild-type mice were administered doses of 475, 237.5, and 118.75 µg of Di-siRNA$^{ApoE}$, respectively. Each group included 3 mice. One month after injection, protein silencing in the hippocampus was quantified and compared to control mice injected with PBS or NTC. As seen in the graph of FIG. 5A and Western blot of FIG. 5B, the novel siRNAs targeting ApoE show protein silencing in vivo at lower doses. Previous reports using oligonucleotides to silence ApoE use sequences that demonstrate an approximately 50% target mRNA and protein silencing after ICV injection of oligonucleotides at a dose of about 400 µg.

2.3 CNS-siRNA$^{ApoE}$ Silences ApoE Throughout the Spinal Cord at Low Doses

Figure 6A:
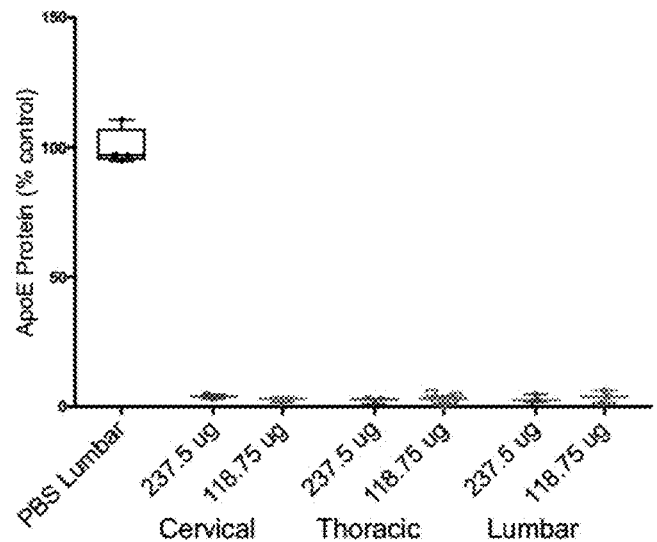
FIG. 6A shows that CNS-siRNA$^{ApoE}$ silences throughout the spinal cord at low doses.
Figure 6B:
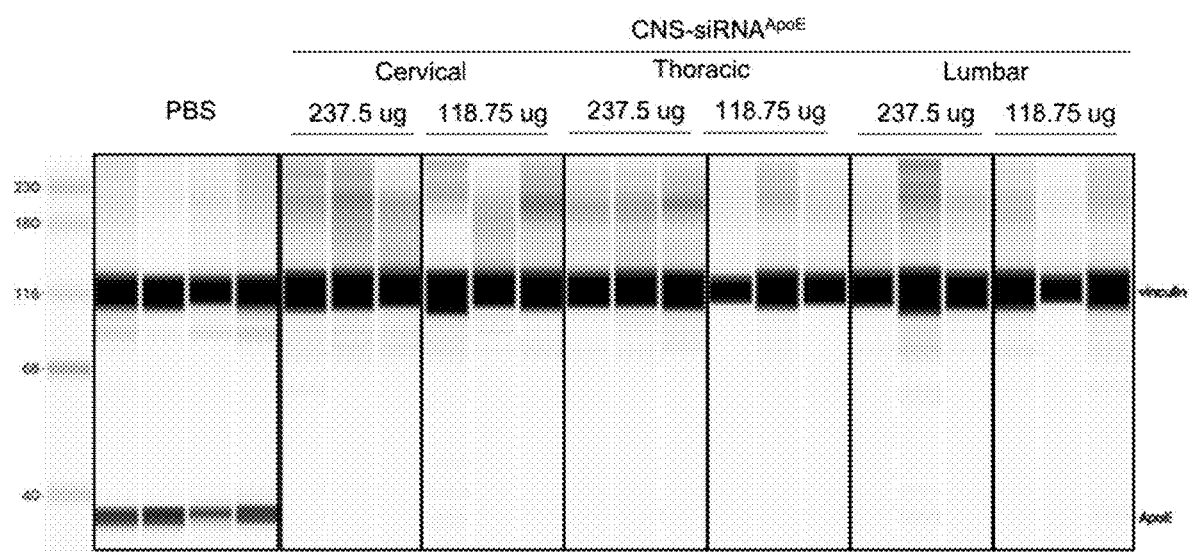
FIG. 6B is a Western blot showing target ApoE (37 kDa) protein silencing as compared to control vinculin (116 kDa).

FIG. 6A is a quantification of protein silencing in the spinal cord 1 month post injection. Di-siRNA$^{ApoE}$ doses: 237.5 and 118.75 µg. FIG. 6B is a Western blot (Protein-Simple) showing target ApoE (37 kDa) protein silencing as compared to control vinculin (116 kDa). Following ICV injection, ApoE 1134 silenced protein expression throughout all regions of the spinal cord (Cervical, Thoracic, Lumbar). Previous silencing of ApoE in the spinal cord had not been shown. The ability to silence spinal cord ApoE has many implications for the treatment of spinal cord related neurodegenerative disorders including Amyotrophic Lateral Sclerosis (ALS).

Figure 7A:
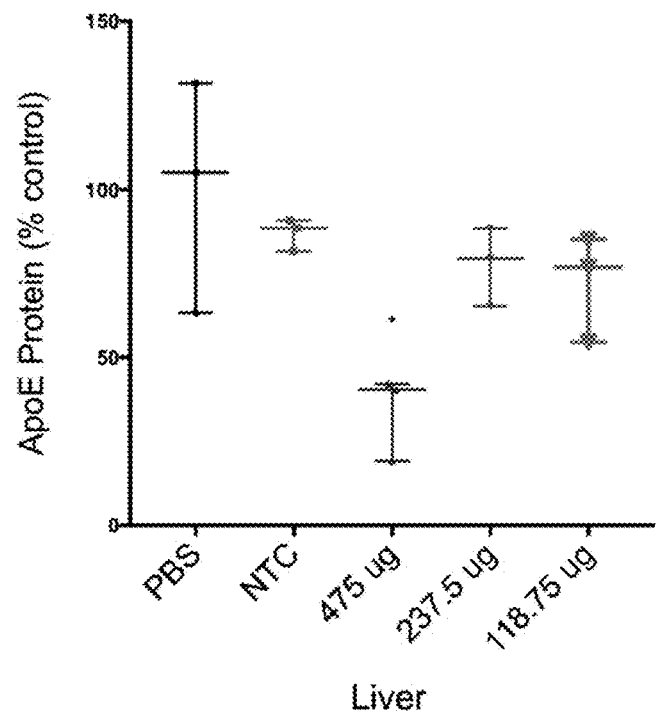
FIGS. 7A-7B show that brain-specific (non-hepatic) silencing of ApoE with CNS-siRNAApoE is possible at lower doses.
Figure 7B:
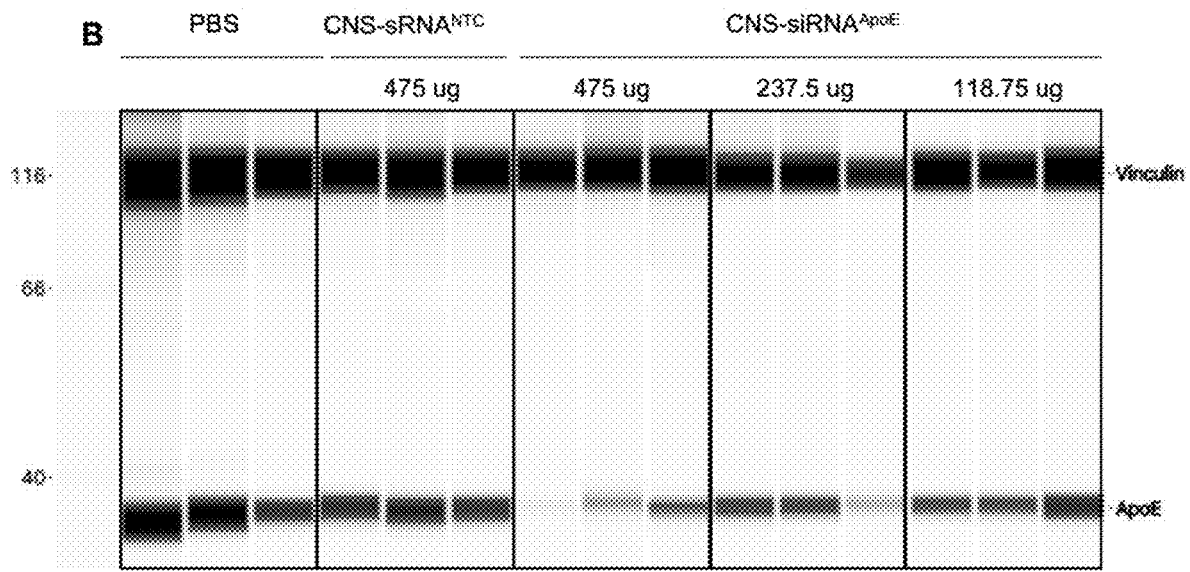

2.4 Brain-Specific (Non-Hepatic) Silencing of ApoE with CNS-siRNA$^{ApoE}$ is Possible at Lower Doses FIG. 7A is a quantification of protein silencing in the liver 1-month post injection. Di-siRNA$^{ApoE}$ doses: 475, 237.5, and 118.75 µg. FIG. 7B is a Western blot (ProteinSimple) showing target ApoE (37 kDa) protein silencing as compared to control vinculin (116 kDa). The dose response to ICV injection of CNS-ApoE showed reduced hepatic protein expression after 475 µg, but no reduction after 237.5 or 118.75 µg. Taken with the silencing data in the brain and spinal cord following the injection of 237.5 and 118.75 µg, this data further suggests that the siRNAs achieve CNS-specific silencing of ApoE. Furthermore, this data also suggests that the two pools of ApoE (CNS and systemic) do not influence each other. Residual hepatic expression does not appear to replenish the silenced CNS (brain or spinal cord) ApoE.

Figure 8A:
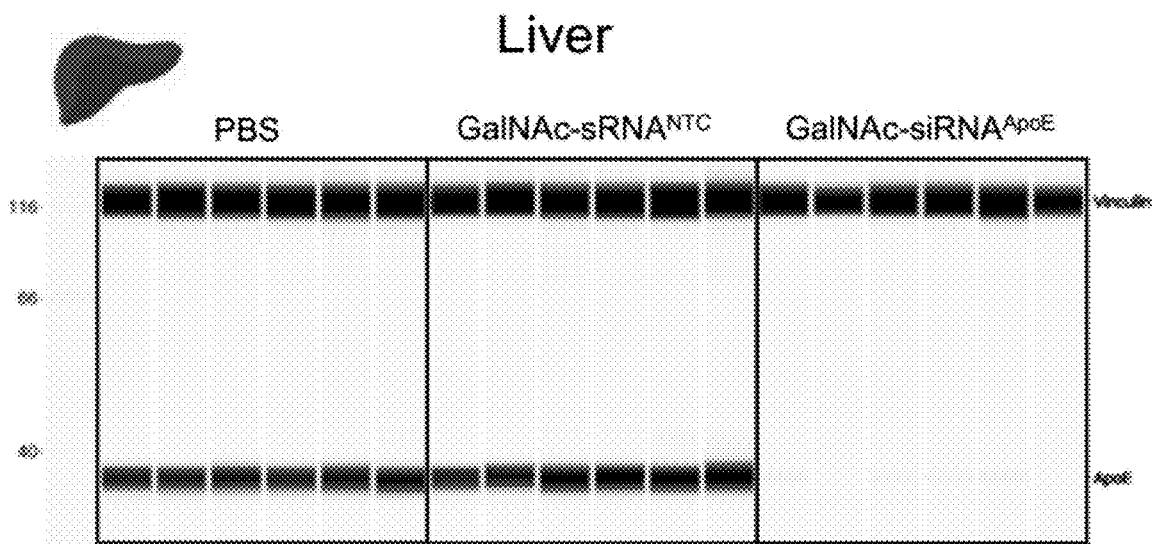
FIGS. 8A-8C show that GalNAc-siRNA$^{ApoE}$ silences protein expression in the liver but has no effect on brain protein.
Figure 8B:
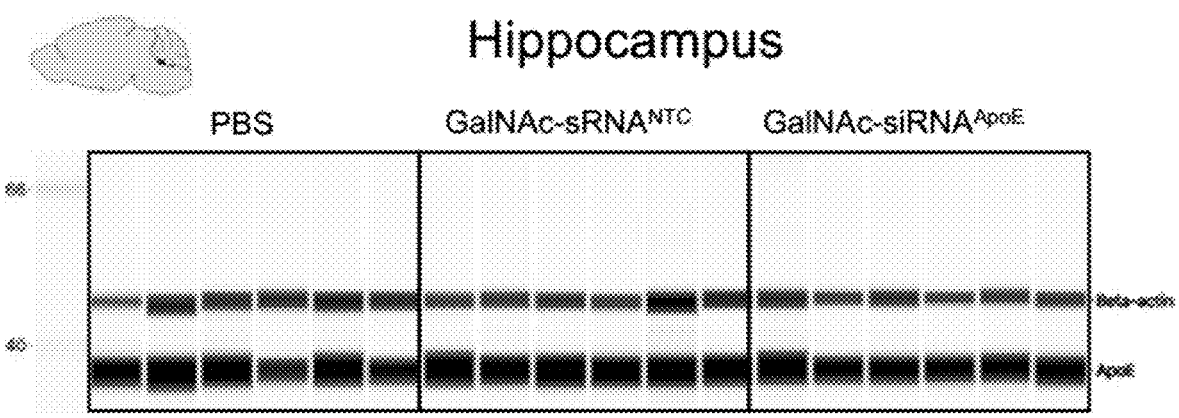
Figure 8C:
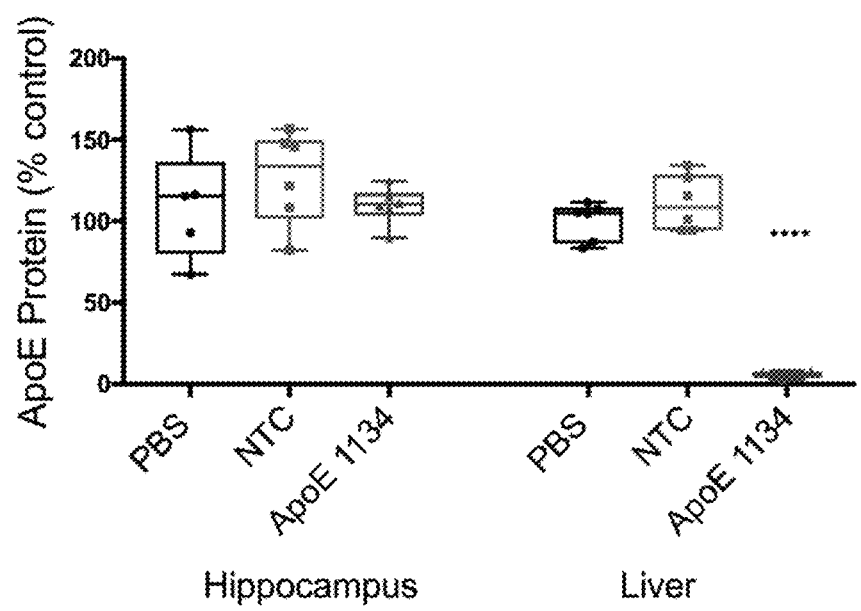

2.5 GalNAc-siRNA$^{ApoE}$ Silences Protein Expression in the Liver but has No Effect on Brain Protein GalNAc conjugates that direct siRNA to hepatocyte liver cells were synthesized and administered to WT mice by subcutaneous injection in the amount of 10 mg/kg. Protein silencing in the liver and hippocampus was quantified 1 month after injection of the GalNAc-siRNA$^{ApoE}$. FIG. 8A is a Western blot (ProteinSimple) showing ApoE protein silencing in the liver vs. control vinculin. FIG. 8B is a Western blot (ProteinSimple) showing no effect on the protein levels in the brain. FIG. 8C is a quantification of protein silencing in the liver and brain. It can be seen that the GalNAc-siRNA$^{ApoE}$ conjugate potently silences hepatic ApoE expression but has no effect on brain ApoE expression. Without being bound to any particular theory, it appears that ApoE produced in the brain does not cross the blood brain barrier and replenish the systemic pool of ApoE even after systemic silencing.

Figure 9A:
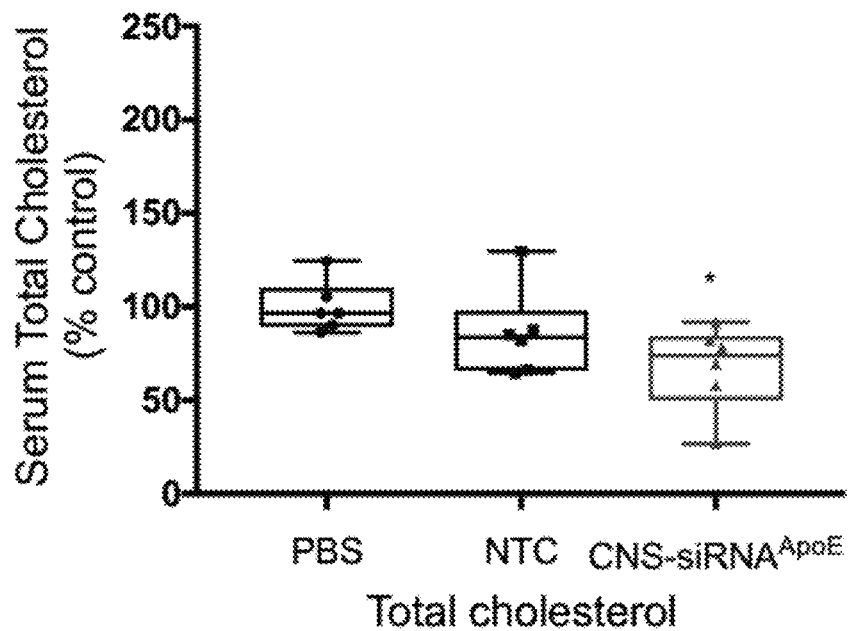
FIGS. 9A-9C show that reducing hepatic ApoE increases serum cholesterol, but silencing only CNS-ApoE does not increase serum cholesterol.
Figure 9B:
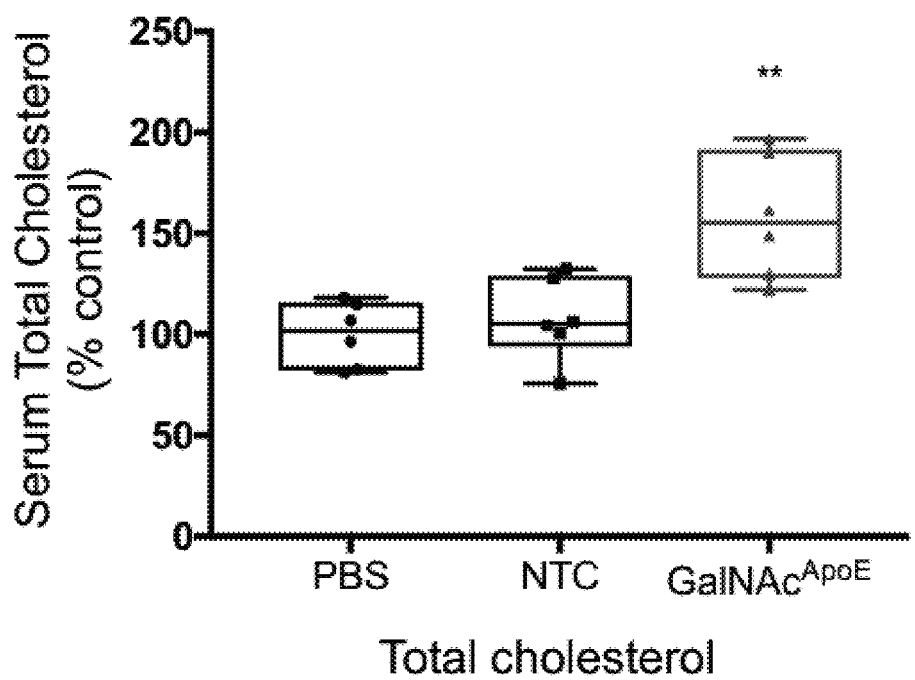
Figure 9C:
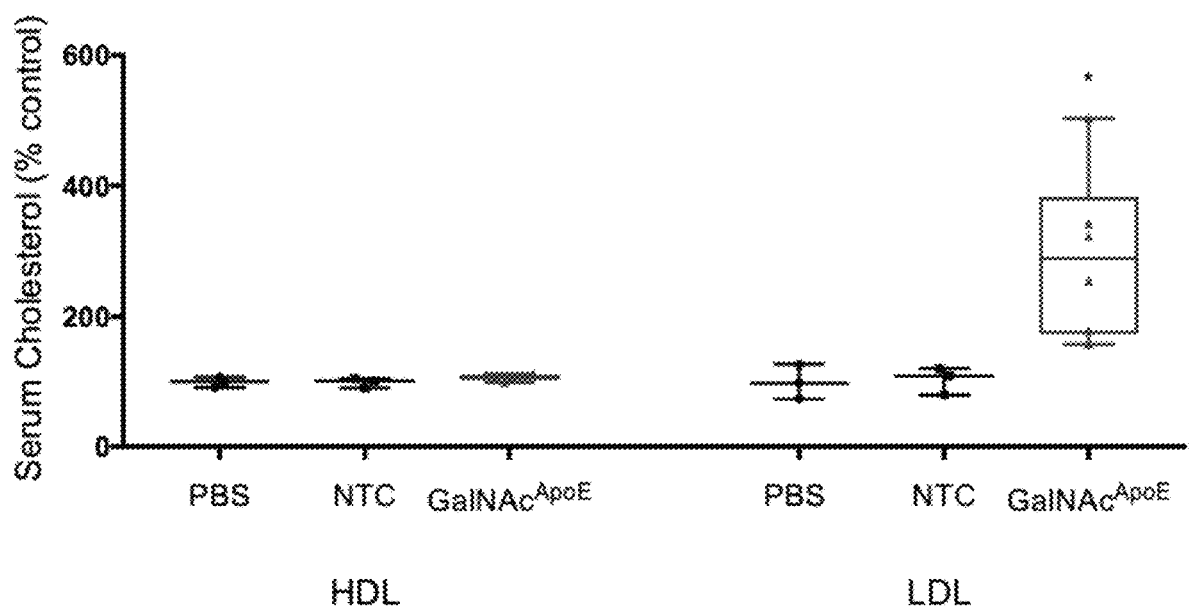

2.6 Reducing Hepatic ApoE Increases Serum Cholesterol, but Silencing Only CNS-ApoE does not Increase Serum Cholesterol A major concern in silencing ApoE as a therapeutic for Alzheimer's disease is the potential effect it could have on systemic cholesterol metabolism. Mice with genetic removal of ApoE develop high systemic cholesterol and aortic atherosclerosis. We show that tissue specific modulation of ApoE in the CNS does not cause an increase in serum cholesterol while systemic modulation causes a significant increase in cholesterol, specifically LDL. This level of discrimination of effects of ApoE silencing on cholesterol has not been previously shown. FIG. 9A depicts a quantification of total serum cholesterol after silencing CNS ApoE. FIG. 9B depicts a quantification of total serum cholesterol after silencing systemic ApoE. FIG. 9C depicts a quantification of cholesterol in LDL and HDL fractions after silencing systemic ApoE.

2.7 CNS and Systemic ApoE Represent Two Distinct Pools of Protein

The use of the ApoE sequences of the present application in combination with tissue-specific chemical conjugates provided evidence that two distinct pools of ApoE exist, i.e., CNS ApoE and systemic ApoE. Without being bound to any particular theory, the data suggest that the two pools of ApoE do not interact, do not influence each other's expression, and do not cross the blood brain barrier. This leads to postulate that one pool of ApoE (CNS or systemic) could be impacting the progression of neuropathology, while the other pool may have little to no effect. FIG. 10A illustrates protein silencing in the brain and liver after injection with CNS-siRNA$^{ApoE}$.

FIG. 10B illustrates silencing in the brain (none) and liver after injection with GalNAc-siRNA$^{ApoE}$.

Example 3. Reversing Off-Target Tissue Silencing of ApoE in the Liver

Figure 16A:
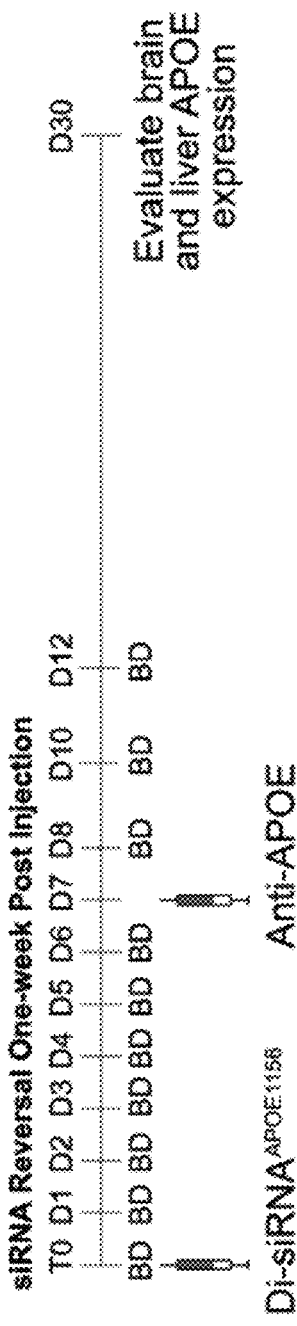
FIGS. 16A-16B illustrate the timeline of an experiment evaluating the reversal of hepatic ApoE silencing by administration of "Anti-ApoE" antagonist compounds in wild-type mice. In the timeline of FIG. 16A, the antagonist was administered one-week post Di-siRNA$^{ApoE1156}$. In the timeline of FIG. 16B, the Di-siRNA$^{ApoE1156}$ were administered simultaneously.
Figure 16B:
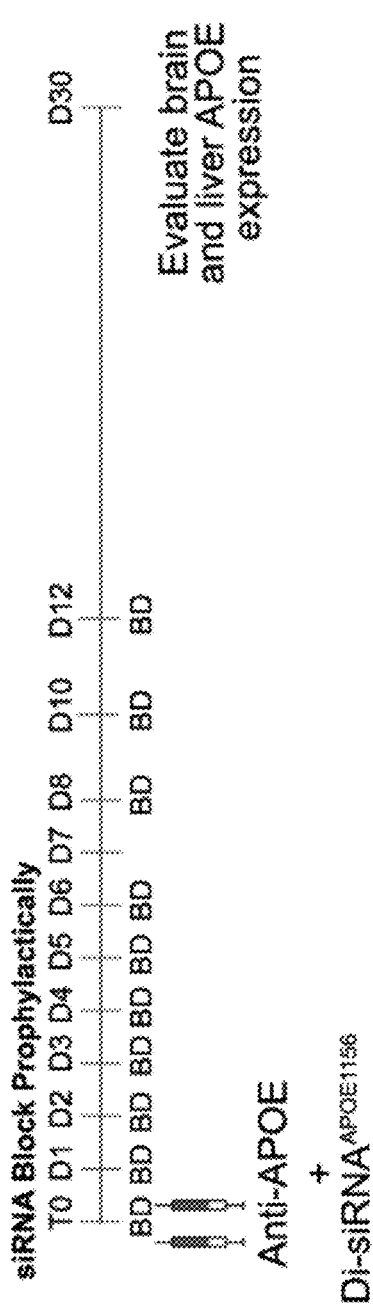

Di-siRNA$^{ApoE1156}$ at a dosage of 475 µg was administered via ICV injection to wild-type mice. Either simultaneously with the administration of the Di-siRNA$^{ApoE1156}$ (FIG. 16B) or one-week post-injection (FIG. 16A), a first group of the animals were treated with GalNac-conjugated 8-mer ASO antagonist, herein labelled "Anti-ApoE 8mer". A second group were treated with 15-mer ASO antagonist, herein labelled "Anti-ApoE 15mer". A third control group were given PBS solution. The AntiApoE or PBS was administered by subcutaneous injection in an amount of 1 mg/kg body weight. Each group included 4-5 mice.

Figure 17A:
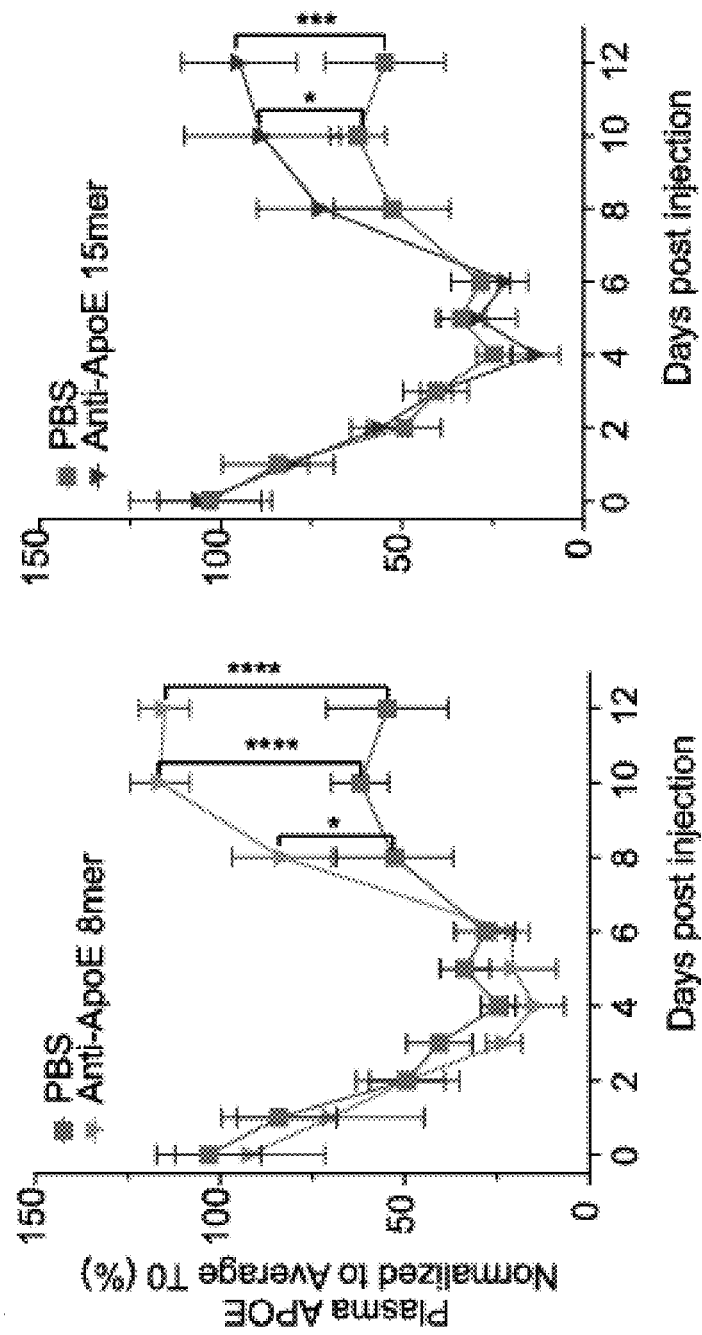
FIGS. 17A-17D report the results of the experiment outlined in FIG. 16. The graphs of FIG. 17A illustrate loss of plasma ApoE expression after treatment with Di-siRNA$^{A}_{POE1156}$ and subsequent rescue of ApoE expression after administration of AntiApoE compounds (vs. PBS). Shown in the graphs of FIG. 17B is a complete block of systemic ApoE silencing by simultaneous dosing of Di-siRNA+Anti-ApoE. The graphs of FIG. 17C illustrate show that rescue of ApoE expression in the liver did not impair ApoE silencing in the brain.
Figure 17B:
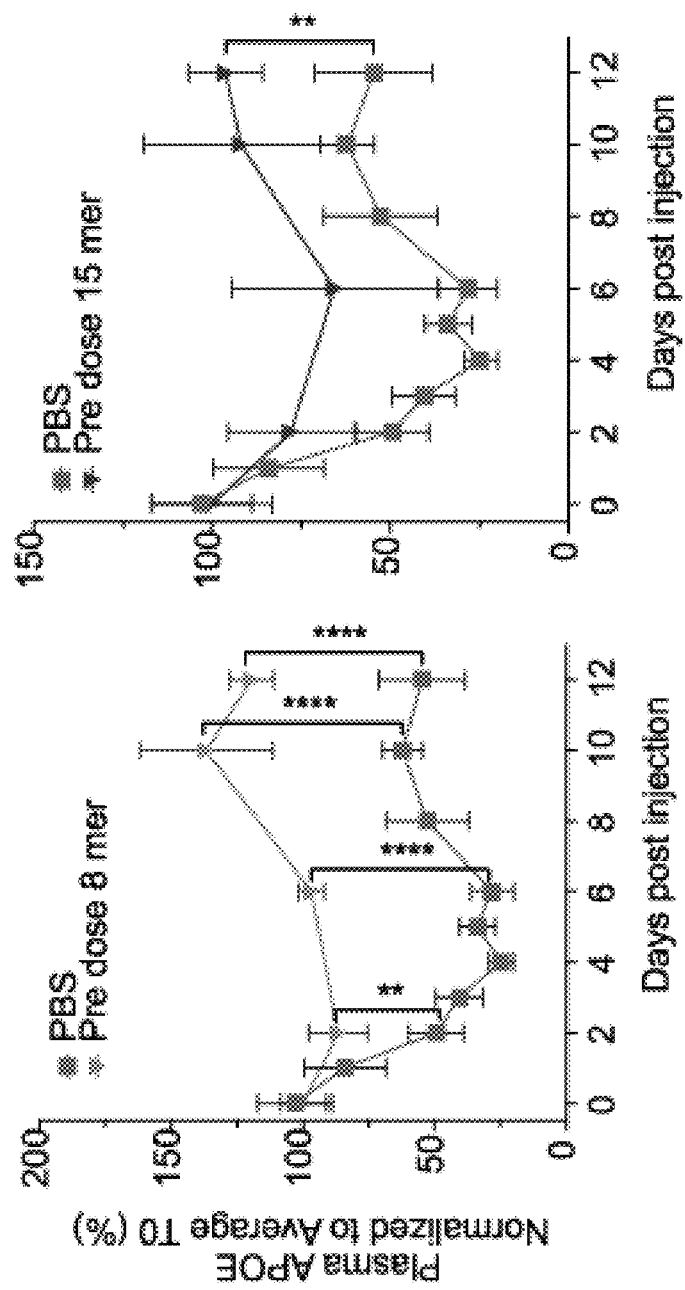
Figure 17C:
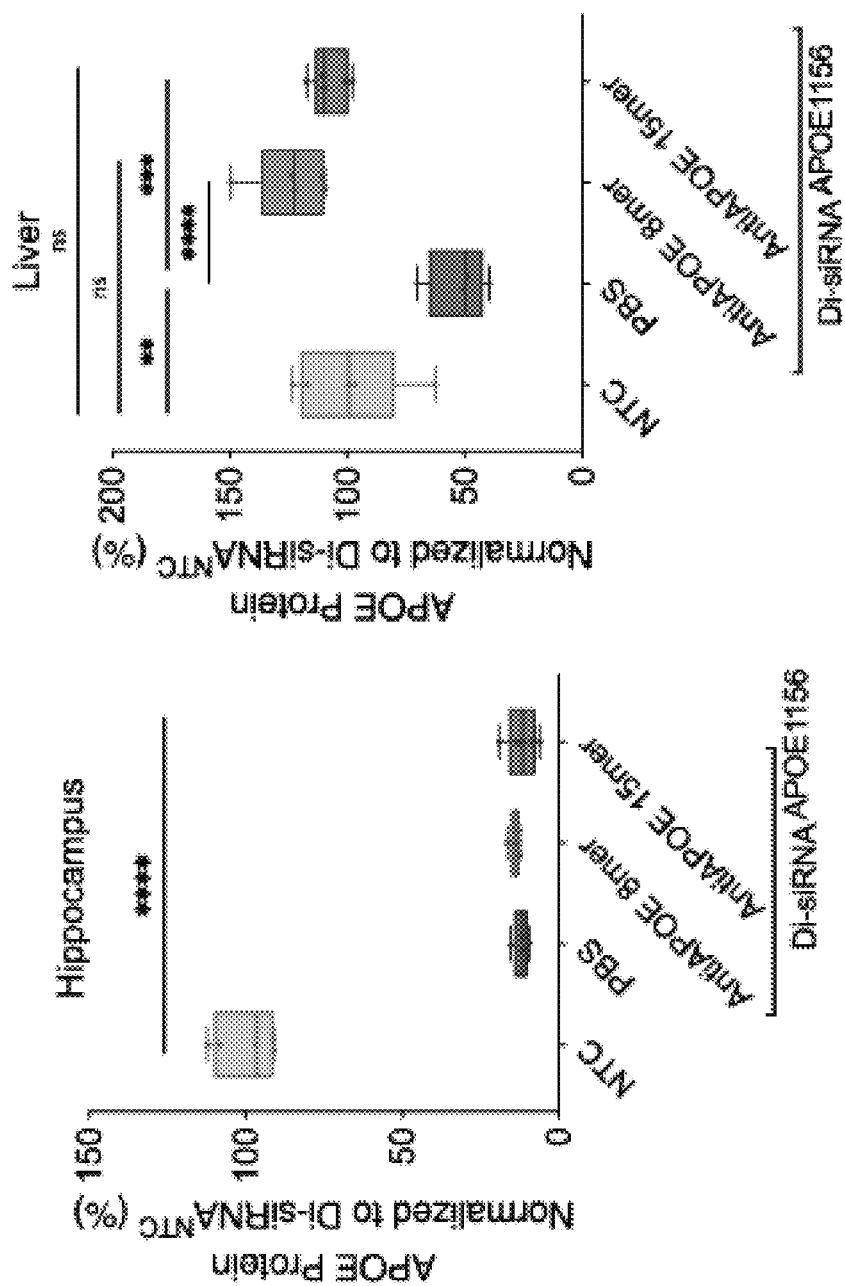
Figure 17D:
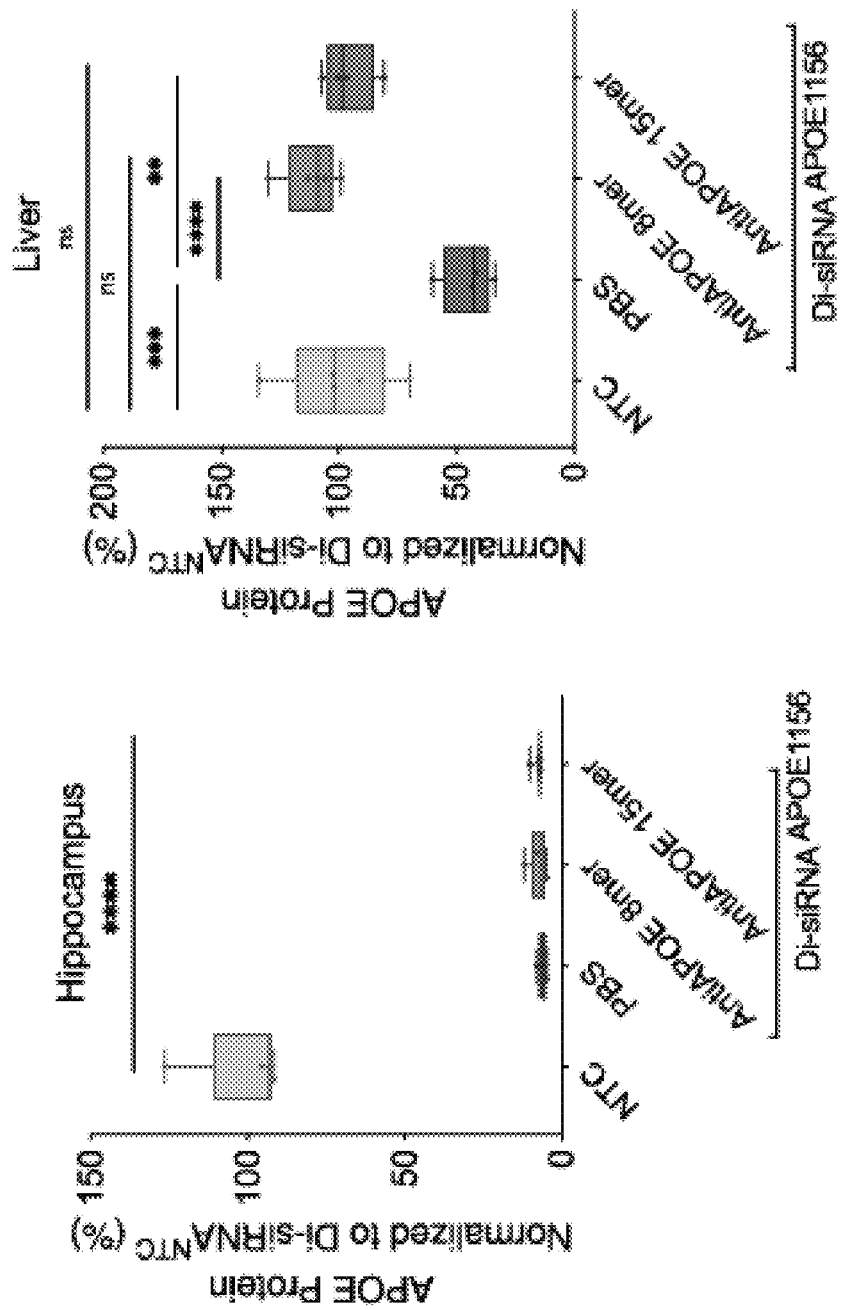

Throughout the course of the experiment plasma ApoE levels were monitored by a Western blot (ProteinSimple) to reflect hepatic expression of ApoE. As illustrated in the graphs of FIG. 17A, loss of plasma ApoE expression followed treatment with Di-siRNA$^{APOE1156}$ and subsequent rescue of ApoE expression was achieved by administration of AntiAPOE antagonist compounds (vs. PBS). When the Di-siRNA$^{ApoE1156}$ and antagonist were administered simultaneously, complete block of systemic ApoE silencing was observed (FIG. 17B). As seen in the graphs of FIG. 17C, the rescue of ApoE expression in the liver did not impair the silencing in the brain. Similarly, and as illustrated in FIG. 17D, the simultaneous administration of Di-siRNA$^{ApoE1156}$ and agonist compounds blocked liver silencing without impacting silencing in the brain.

Example 4. Anti-siRNAs to Achieve Tissue Selective siRNA Silencing

The aim of this planned study is to evaluate the efficacy of anti-siRNAs in achieving tissue selective siRNA silencing when combined with conjugated siRNAs targeting muscle, lung, and heart.

The following groups will be used:
DCA-siRNA
DCA-siRNA+GalNAc anti-siRNA
EPA-siRNA
EPA-siRNA+GalNAc anti-siRNA
PBS control Mice will be injected on Day 1 with either PBS, DCA-siRNA, DCA-siRNA+GalNAc anti-siRNA, EPA-siRNA, or EPA-siRNA+anti-siRNA, subcutaneously. On Day 7, silencing will be evaluated in systemic organs.

The expected results are maintained potent silencing in target tissues such as the muscle and lung while blocking the siRNA silencing effect in other organs including the liver. Any combination of conjugated siRNAs can be used to achieve tissue specific silencing. For example, co-injection of a DCA-siRNA conjugate with a GalNAc anti-siRNA conjugate will demonstrate maintained silencing in the muscle, heart, and lung tissue, while reducing or eliminating off-target silencing in the liver or kidney. Similarly, co-injection of a EPA-siRNA conjugate with a GalNAc anti-siRNA conjugate will demonstrate maintained silencing in the lung and other tissues, while reducing or eliminating off-target silencing in the liver or kidney.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), CURRENT PROTOCOLS IN MOLECULAR BIOLOGY, John Wiley &Sons, N Y (1993);

Ausubel, F. M. et al. eds., SHORT PROTOCOLS IN MOLECULAR BIOLOGY (4th Ed. 1999) John Wiley & Sons, NY. (ISBN 0-471-32938-X);

CONTROLLED DRUG BIOAVAILABILITY, DRUG PRODUCT DESIGN AND PERFORMANCE, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, New York, (1999);

Goodson, in MEDICAL APPLICATIONS OF CONTROLLED RELEASE, vol. 2, pp. 115-138 (1984);

Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, N Y (1990);

Lu and Weiner eds., CLONING AND EXPRESSION VECTORS FOR GENE FUNCTION ANALYSIS (2001) BioTechniques Press. Westborough, MA. 298 pp. (ISBN 1-881299-21-X).

MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V. 2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).

SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A therapeutic combination of drugs for the treatment or management of a neurodegenerative disease, the combination comprising:
   a first conjugate comprising an RNA silencing agent inhibiting the expression of Apoliprotein E (ApoE) gene, the RNA silencing agent comprising a divalent siRNA (Di-siRNA) comprising two siRNAs conjugated to one another via a linker comprising 1-4 repeat units of ethylene glycol, and a first targeting agent that targets the first conjugate to the central nervous system, and
   a second conjugate comprising an antagonist of the RNA silencing agent and a second targeting agent that targets the second conjugate to an off-target tissue, wherein the second conjugate is configured to selectively inhibit, reduce, or eliminate the activity of the RNA silencing agent to inhibit the expression of the ApoE gene in the off-target tissue without impairing the activity of the RNA silencing agent in the central nervous system.

2. The therapeutic combination of drugs of claim 1, wherein the first conjugate and second conjugate are in separate pharmaceutical compositions.

3. The therapeutic combination of drugs of claim 1, wherein the two siRNAs comprise an RNA molecule comprising 15 to 35 bases in length, comprising a region of complementarity which is sufficiently complementary to 5' GUUUAAUAAAGAUUCACCAAGUUUCACGCAAA 3' (SEQ ID NO: 1) to direct target-specific silencing.

4. The therapeutic combination of drugs of claim 1, wherein the second targeting agent comprises a GalNac.

5. The therapeutic combination of drugs of claim 1, wherein the antagonist to the RNA silencing agent comprises one or more locked nucleic acids.

6. The therapeutic combination of drugs of claim 1, wherein the antagonist to the RNA silencing agent comprises 8 to 20 bases in length.

7. The therapeutic combination of drugs of claim 1, wherein the off-target tissue comprises a clearance tissue.

8. A kit for the treatment or management of a neurodegenerative disease, the kit comprising:
   a first pharmaceutically acceptable composition of a first conjugate comprising an RNA silencing agent inhibiting the expression of Apoliprotein E (ApoE) gene, the silencing agent comprising a divalent siRNA (Di-siRNA) comprising two siRNAs conjugated to one another via a linker comprising 1-4 repeat units of ethylene glycol, and a first targeting agent that targets the first conjugate to a central nervous system,
   a second pharmaceutically acceptable composition of a second conjugate comprising an antagonist of the RNA silencing agent and a second targeting agent that targets the second conjugate to a tissue outside the central nervous system, wherein the second conjugate is configured to selectively inhibit, reduce, or eliminate the activity of the RNA silencing agent inhibit the expression of the ApoE gene in the tissue outside the central nervous system without impairing the activity of the RNA silencing agent in the central nervous system, and
   instructions for the administration of the first composition and second composition for treatment of a neurodegenerative disease.

9. A combination comprising:
   a first conjugate comprising an RNA silencing agent inhibiting the expression of Apoliprotein E (ApoE) gene, the silencing agent comprising a divalent siRNA (Di-siRNA) comprising two siRNAs conjugated to one another via a linker comprising 1-4 repeat units of ethylene glycol, and a first targeting agent that targets the first conjugate to a target tissue, and a second conjugate comprising an anti-RNA silencing agent and a second targeting agent that targets the second conjugate to an off-target tissue;

wherein the second conjugate is configured to selectively inhibit, reduce, or eliminate the activity of the RNA silencing agent to inhibit the expression of the ApoE gene in the off-tissue without impairing the activity of the RNA silencing agent in the target tissue.

10. The combination of claim 9, wherein the first conjugate and second conjugate are in separate pharmaceutical compositions.

11. The combination of claim 9, wherein the first targeting agent comprises cholesterol, eicosapentaenoic acid (EPA), docosahexaenoic acid (DHA), or docosanoic acid (DCA).

12. The combination of claim 9, wherein the anti-RNA silencing agent comprises a single-stranded oligonucleotide sufficiently complementary to the RNA silencing agent to inhibit, reduce, or eliminate the activity of the RNA silencing agent.

13. The combination of claim 9, wherein the second targeting agent comprises a GalNAc.

14. The combination of claim 9, wherein the anti-RNA silencing agent comprises 8 to 20 bases in length.

15. The combination of claim 9, wherein the off-target tissue comprises a clearance tissue.

* * * * *

SEQUENCE LISTING

```
<160> NUMBER OF SEQ ID NOS: 51

<210> SEQ ID NO 1
<211> LENGTH: 32
<212> TYPE: RNA
<213> ORGANISM: Unknown
<220> FEATURE:
<223> OTHER INFORMATION: Description of Unknown:
      Target sequence

<400> SEQUENCE: 1
guuuaauaaa gauucaccaa guuucacgca aa                                         32

<210> SEQ ID NO 2
<211> LENGTH: 15
<212> TYPE: RNA
<213> ORGANISM: Unknown
<220> FEATURE:
<223> OTHER INFORMATION: Description of Unknown:
      Target sequence

<400> SEQUENCE: 2
gauucaccaa guuua                                                            15

<210> SEQ ID NO 3
<211> LENGTH: 15
<212> TYPE: RNA
<213> ORGANISM: Unknown
<220> FEATURE:
```

```
<223> OTHER INFORMATION: Description of Unknown:
      Target sequence

<400> SEQUENCE: 3
caaguuucac gcaaa                                                          15

<210> SEQ ID NO 4
<211> LENGTH: 14
<212> TYPE: RNA
<213> ORGANISM: Unknown
<220> FEATURE:
<223> OTHER INFORMATION: Description of Unknown:
      Target sequence

<400> SEQUENCE: 4
caaguuucac gcaa                                                           14

<210> SEQ ID NO 5
<211> LENGTH: 32
<212> TYPE: RNA
<213> ORGANISM: Mus musculus

<400> SEQUENCE: 5
guuuaauaaa gauucaccaa guuucacgca aa                                       32

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuggauaugg auguuguugc ag                                                  22

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaacaacau ccauauccaa                                                     20

<210> SEQ ID NO 8
<211> LENGTH: 31
<212> TYPE: RNA
<213> ORGANISM: Mus musculus

<400> SEQUENCE: 8
ccuugcuuaa uaaagauucu ccgagcacau u                                        31

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ucucggagaa ucuuuauuaa gc                                                  22
```

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuaauaaaga uucuccgaga                                                    20

<210> SEQ ID NO 11
<211> LENGTH: 30
<212> TYPE: RNA
<213> ORGANISM: Homo sapiens

<400> SEQUENCE: 11
guuuaauaaa gauucaccaa guuucacgca                                         30

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uaaacuuggu gaaucuuuau                                                    20

<210> SEQ ID NO 13
<211> LENGTH: 32
<212> TYPE: RNA
<213> ORGANISM: Homo sapiens

<400> SEQUENCE: 13
guuuaauaaa gauucaccaa guuucacgca aa                                      32

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuugcgugaa acuuggugaa                                                    20

<210> SEQ ID NO 15
<211> LENGTH: 30
<212> TYPE: DNA
<213> ORGANISM: Homo sapiens

<400> SEQUENCE: 15
caggcaggaa gatgaaggtt ctgtgggctg                                         30

<210> SEQ ID NO 16
<211> LENGTH: 20
<212> TYPE: RNA
<213> ORGANISM: Homo sapiens

<400> SEQUENCE: 16
aggaagauga agguucugug                                                    20

<210> SEQ ID NO 17
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gaugaagguu cugug                                                    15

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cacagaaccu ucaucuuccu                                               20

<210> SEQ ID NO 19
<211> LENGTH: 30
<212> TYPE: DNA
<213> ORGANISM: Homo sapiens

<400> SEQUENCE: 19
tcctggggtg gaccctagtt taataaagat                                    30

<210> SEQ ID NO 20
<211> LENGTH: 20
<212> TYPE: RNA
<213> ORGANISM: Homo sapiens

<400> SEQUENCE: 20
ggguggaccc uaguuuaaua                                               20

<210> SEQ ID NO 21
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gacccuaguu uaaua                                                    15

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uauuaaacua ggguccaccc                                               20

<210> SEQ ID NO 23
<211> LENGTH: 30
<212> TYPE: DNA
<213> ORGANISM: Homo sapiens

<400> SEQUENCE: 23
ggggtggacc ctagtttaat aaagattcac                              30

<210> SEQ ID NO 24
<211> LENGTH: 20
<212> TYPE: RNA
<213> ORGANISM: Homo sapiens

<400> SEQUENCE: 24
ggacccuagu uuaauaaaga                                         20

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cuaguuuaau aaaga                                              15

<210> SEQ ID NO 26
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ucuuuauuaa acuagggucc                                         20

<210> SEQ ID NO 27
<211> LENGTH: 30
<212> TYPE: DNA
<213> ORGANISM: Homo sapiens

<400> SEQUENCE: 27
tggaccctag tttaataaag attcaccaag                              30

<210> SEQ ID NO 28
<211> LENGTH: 20
<212> TYPE: RNA
<213> ORGANISM: Homo sapiens

<400> SEQUENCE: 28
ccuaguuuaa uaaagauuca                                         20

<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuuaauaaag auuca                                              15

<210> SEQ ID NO 30
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 30
ugaaucuuua uuaaacuagg                                                      20

<210> SEQ ID NO 31
<211> LENGTH: 30
<212> TYPE: DNA
<213> ORGANISM: Homo sapiens

<400> SEQUENCE: 31
ctagtttaat aaagattcac caagtttcac                                           30

<210> SEQ ID NO 32
<211> LENGTH: 20
<212> TYPE: RNA
<213> ORGANISM: Homo sapiens

<400> SEQUENCE: 32
uuaauaaaga uucaccaagu                                                      20

<210> SEQ ID NO 33
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aaagauucac caagu                                                           15

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
acuuggugaa ucuuuauuaa                                                      20

<210> SEQ ID NO 35
<211> LENGTH: 30
<212> TYPE: DNA
<213> ORGANISM: Homo sapiens

<400> SEQUENCE: 35
gtttaataaa gattcaccaa gtttcacgca                                           30

<210> SEQ ID NO 36
<211> LENGTH: 20
<212> TYPE: RNA
<213> ORGANISM: Homo sapiens

<400> SEQUENCE: 36
uaaagauuca ccaaguuuca                                                      20

<210> SEQ ID NO 37
<211> LENGTH: 15
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 37
auucaccaag uuuca                                                          15

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugaaacuugg ugaaucuuua                                                     20

<210> SEQ ID NO 39
<211> LENGTH: 31
<212> TYPE: DNA
<213> ORGANISM: Mus musculus

<400> SEQUENCE: 39
tgtcctgcaa caacatccat atccagccag g                                        31

<210> SEQ ID NO 40
<211> LENGTH: 31
<212> TYPE: DNA
<213> ORGANISM: Mus musculus

<400> SEQUENCE: 40
ccttgcttaa taaagattct ccgagcacat t                                        31

<210> SEQ ID NO 41
<211> LENGTH: 32
<212> TYPE: DNA
<213> ORGANISM: Homo sapiens

<400> SEQUENCE: 41
gtttaataaa gattcaccaa gtttcacgca aa                                       32

<210> SEQ ID NO 42
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
aacauccaua uccaa                                                          15

<210> SEQ ID NO 43
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aacauccaua uccaa                                                          15

<210> SEQ ID NO 44
```

<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aaagauucuc cgaga                                                     15

<210> SEQ ID NO 45
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aaagauucuc cgaga                                                     15

<210> SEQ ID NO 46
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gauucaccaa guuua                                                     15

<210> SEQ ID NO 47
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
caaguuucac gcaaa                                                     15

<210> SEQ ID NO 48
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gauucaccaa guuua                                                     15

<210> SEQ ID NO 49
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
caaguuucac gcaaa                                                     15

<210> SEQ ID NO 50
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 50

Gln Gln Gln Gln Gln
1               5

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: See specification as filed for detailed
      description of substitutions and preferred embodiments

<400> SEQUENCE: 51

Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln
        35
```